(12) United States Patent

Ebata

(10) Patent No.: US 9,936,859 B2
(45) Date of Patent: Apr. 10, 2018

(54) MEDICAL SYSTEM

(71) Applicant: OLYMPUS CORPORATION, Tokyo (JP)

(72) Inventor: Sadao Ebata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 460 days.

(21) Appl. No.: 14/588,625

(22) Filed: Jan. 2, 2015

(65) Prior Publication Data

US 2015/0119639 A1 Apr. 30, 2015

Related U.S. Application Data

(63) Continuation of application No. PCT/JP2013/069229, filed on Jul. 8, 2013.

(30) Foreign Application Priority Data

Jul. 12, 2012 (JP) ................................. 2012-156620

(51) Int. Cl.
*A61B 1/00* (2006.01)
*A61B 1/018* (2006.01)
(Continued)

(52) U.S. Cl.
CPC .......... *A61B 1/0005* (2013.01); *A61B 1/0002* (2013.01); *A61B 1/00006* (2013.01);
(Continued)

(58) Field of Classification Search
USPC ................ 600/103, 114, 115, 116, 117, 121, 600/122–125
See application file for complete search history.

(56) References Cited

U.S. PATENT DOCUMENTS 6,092,722 A * 7/2000 Heinrichs .......... A61B 1/00016
235/375
6,436,032 B1 * 8/2002 Eto .................... A61B 1/00059
600/117
(Continued)

FOREIGN PATENT DOCUMENTS

DE 196 29 646 A1 1/1998
DE 20 2007 015 093 U1 2/2008
(Continued)

OTHER PUBLICATIONS

Extended Supplementary European Search Report dated Feb. 26, 2016 from related European Application No. 13 81 6424.9.
(Continued)

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

A medical system includes an endoscope apparatus including a plurality of insertion portions and a main unit supporting them; a sheath unit attachable to a biological subject and having a through-hole through which the insertion portions can be passed; a monitor; barcodes from which the insertion portions issue identification information; an identification-signal generating unit that acquires the identification information from the barcodes and outputs this to the main unit every time the insertion portions pass through the through-hole; wherein the main unit includes an image selector that displays, on the monitor, an image acquired by the insertion portion identified by the main unit as having being have passed through the sheath unit on the basis of the identification information from the identification-signal generating unit.

1 Claim, 36 Drawing Sheets

(51) Int. Cl.

| | | |
|---|---|---|
| *A61B 1/045* | (2006.01) | |
| *A61B 1/06* | (2006.01) | |
| *A61B 17/00* | (2006.01) | |
| *A61B 1/313* | (2006.01) | |
| *A61B 1/01* | (2006.01) | |
| *A61B 90/90* | (2016.01) | |
| *A61B 17/34* | (2006.01) | |
| *A61B 90/96* | (2016.01) | |
| *A61B 90/98* | (2016.01) | |

(52) U.S. Cl.
CPC ...... *A61B 1/00036* (2013.01); *A61B 1/00052* (2013.01); *A61B 1/00055* (2013.01); *A61B 1/00059* (2013.01); *A61B 1/00105* (2013.01); *A61B 1/00135* (2013.01); *A61B 1/00154* (2013.01); *A61B 1/01* (2013.01); *A61B 1/018* (2013.01); *A61B 1/045* (2013.01); *A61B 1/0676* (2013.01); *A61B 1/313* (2013.01); *A61B 17/00234* (2013.01); *A61B 90/90* (2016.02); *A61B 90/96* (2016.02); *A61B 90/98* (2016.02); *A61B 2017/0034* (2013.01); *A61B 2017/00115* (2013.01); *A61B 2017/00243* (2013.01); *A61B 2017/3445* (2013.01)

(56) References Cited

U.S. PATENT DOCUMENTS

| | | | | |
|---|---|---|---|---|
| 6,646,541 B1* | 11/2003 | Wang | ............... | A61B 17/00 340/3.54 |
| 6,716,219 B1* | 4/2004 | Koch | ............... | A61F 9/00736 422/300 |
| 6,847,490 B1* | 1/2005 | Nordstrom | ......... | A61B 1/00062 359/642 |
| 7,129,472 B1* | 10/2006 | Okawa | ............... | A61B 1/00059 250/216 |
| 2001/0029315 A1* | 10/2001 | Sakurai | .......... | A61B 17/320068 600/101 |
| 2002/0038102 A1* | 3/2002 | McFarlin | ........... | A61B 17/1626 604/30 |
| 2002/0115917 A1* | 8/2002 | Honda | .................. | A61B 17/00 600/301 |
| 2005/0004559 A1* | 1/2005 | Quick | ................... | A61B 10/02 606/1 |
| 2005/0043828 A1* | 2/2005 | Tanaka | ........... | A61B 17/320068 700/83 |
| 2005/0143724 A1* | 6/2005 | El-Galley Rizk | .. | A61B 18/1402 606/34 |
| 2005/0148819 A1* | 7/2005 | Noguchi | ............ | A61B 1/00059 600/133 |
| 2007/0085686 A1* | 4/2007 | Oz | ..................... | A61B 1/00016 340/572.8 |
| 2007/0299387 A1* | 12/2007 | Williams | ........... | A61B 1/00052 604/22 |
| 2008/0064925 A1* | 3/2008 | Gill | .................... | A61B 1/00059 600/109 |
| 2008/0091065 A1* | 4/2008 | Oshima | .................. | A61B 1/045 600/109 |
| 2010/0071736 A1* | 3/2010 | Watanabe | .......... | A61B 1/00006 134/56 R |
| 2011/0084835 A1* | 4/2011 | Whitehouse | ....... | A61B 1/00059 340/540 |
| 2012/0201433 A1* | 8/2012 | Iwasaki | .............. | A61B 1/00009 382/128 |
| 2013/0141557 A1* | 6/2013 | Kawata | .............. | A61B 1/00006 348/65 |
| 2013/0150668 A1* | 6/2013 | Kanno | ............... | A61B 1/00059 600/109 |
| 2014/0171785 A1* | 6/2014 | Zino | ................ | A61B 17/00234 600/424 |
| 2015/0088030 A1* | 3/2015 | Taylor | .................... | A61B 5/407 600/554 |
| 2016/0354170 A1* | 12/2016 | Ogawa | .................... | A61B 34/70 |
| 2016/0375273 A1* | 12/2016 | Hirai | ...................... | A61B 17/29 606/29 |

FOREIGN PATENT DOCUMENTS

| | | | | |
|---|---|---|---|---|
| DE | 202007015093 U1 * | 2/2008 | ............ | A61B 1/018 |
| JP | 11-000310 A | 1/1999 | | |
| JP | 2004-290380 A | 10/2004 | | |
| JP | 2009-077763 A | 4/2009 | | |
| JP | 2009-077765 A | 4/2009 | | |
| JP | 2009-112644 A | 5/2009 | | |
| JP | 2009-207793 A | 9/2009 | | |
| JP | 4472759 B2 | 6/2010 | | |
| JP | 2010-158303 A | 7/2010 | | |

OTHER PUBLICATIONS

Chinese Office Action dated Dec. 28, 2015 from related Chinese Patent Application No. 201380036552.1, together with an English language translation.
International Search Report dated Aug. 20, 2013 issued in PCT/JP2013/069229.
English Abstract of JP 2008-194457 A, dated Aug. 28, 2008.

* cited by examiner

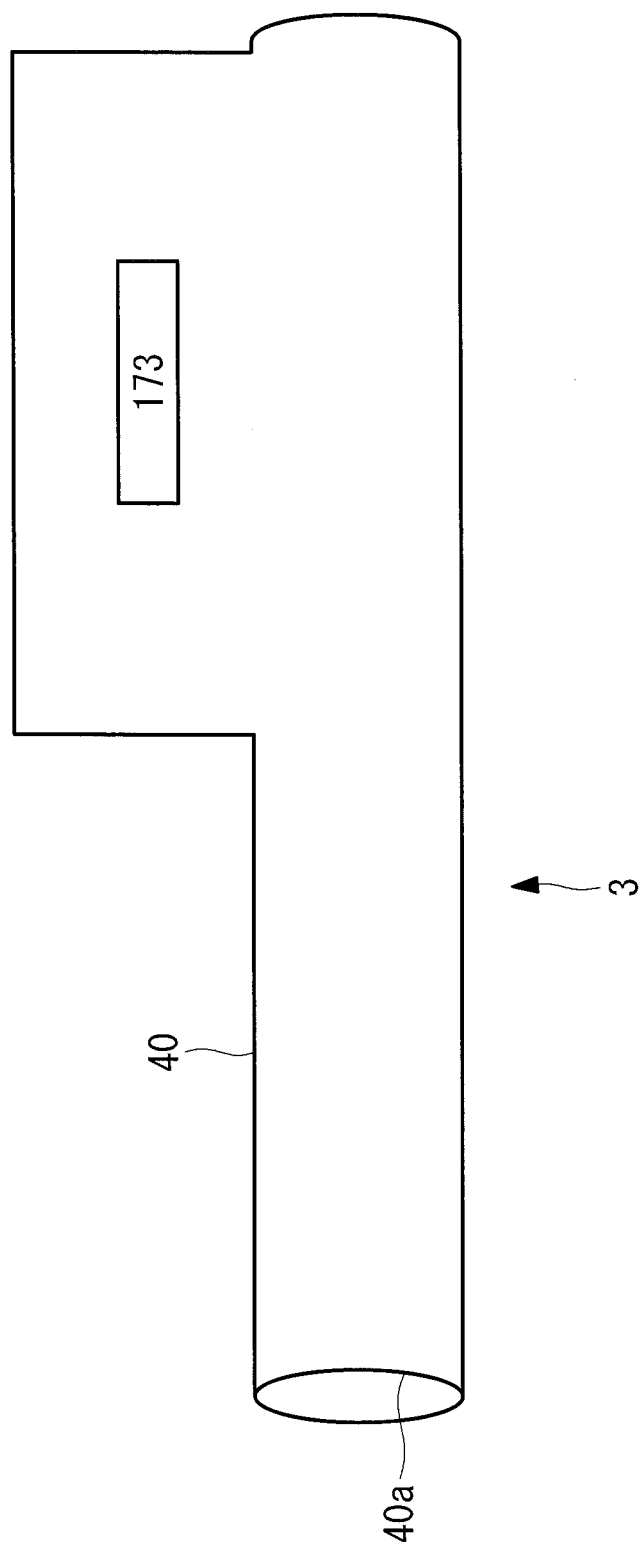

MEDICAL SYSTEM

CROSS-REFERENCE TO RELATED APPLICATIONS

This application is a continuation application of PCT/JP2013/069229, filed on Jul. 8, 2013, the contents of which are incorporated herein by reference.

This application is based on Japanese Patent Application No. 2012-156620, filed on Jul. 12, 2012, the contents of which are incorporated herein by reference.

TECHNICAL FIELD

The present invention relates to a medical system.

BACKGROUND ART

There are known endoscopic surgical procedures carried out on the heart, involving examination and various treatments to be performed by inserting an endoscope near the ensiform cartilage into the pericardium. An advantage of such procedures is that the burden on patients is extremely low because the operation is less invasive and leaves only a small surgical wound compared with conventional medical treatment for cardiac diseases conducted surgically by opening the chest.

To achieve minimum invasiveness in an endoscopic surgical procedure that approaches the pericardium, it is desirable to make an extremely small incision through which a device is inserted. Specifically, a sheath is inserted into a small incision, and then an endoscope or treatment device is inserted into the pericardium through the sheath for examination and various treatments.

In such a surgical procedure, various types of endoscopes or treatment devices are inserted into the pericardium. For example, endoscopes include side-viewing endoscopes and forward-viewing endoscopes, which have different optical systems; flexible scopes and rigid scopes, which have insertion portions with different hardnesses and shapes; and ultrasonic endoscopes, which have optical examination as well as ultrasonic diagnosis functions. These are used in accordance with the situation during surgery and, in some cases, the inserted endoscope is switched frequently.

Meanwhile, the processor that drives the endoscope is often not suited for driving different types of endoscopes. One reason for this is that, for example, a large processor would be required. In such a case, processors used exclusively with individual endoscopes are required, and, thus, there is a need to provide dedicated image display devices for the individual processors. For instance, in a case where an image display device supporting different video formats is used, the connection between the processor and the image display device has to be switched every time the inserted endoscope is switched.

Thus, in the case where a plurality of endoscopes are used, a video-signal switching device for an endoscope system that first collects the video signals output from individual processors and then selects and switches the video signal to be input to an image display device has been proposed (for example, refer to PTL 1).

CITATION LIST

Patent Literature

{PTL 1}
Japanese Unexamined Patent Application, Publication No. HEI-11-310

SUMMARY OF INVENTION

Technical Problem

However, the video-signal switching device of the endoscope system described in PTL 1 does not require dedicated image display devices for the processors because the images output to the image display device can be switched, but the image to be displayed on the image display device needs to be manually switched. It is ok if the image display device is always accessible to the operator, but this is not always true; thus, there are circumstances in which the video signal is not immediately switched every time the inserted endoscope is switched. With a large system resulting from advanced, complicated surgery, the distance between the operator and the image display device may end up being large. Thus, every time the endoscope or treatment tool to be used is switched, the image information displayed on the display unit in association therewith is not immediately switched.

The present invention is to provide a medical system in which, every time an insertion portion of an image acquisition device or a treatment device to be inserted into a body cavity in a biological subject is switched, it is possible to readily switch information of the insertion portion displayed on a display unit.

Solution to Problem

An aspect of the present invention provides a medical system including an outer sleeve that has one end and another end, that has a through-hole formed from the one end to the another end, and that is attachable to the biological subject while the one end is inserted into the biological subject;

a medical device including a plurality of insertion portions that are inserted into a body cavity in the biological subject through the through-hole and a main unit that supports the plurality of insertion portions; a display unit on which insertion-portion unique information serving as unique information of each insertion portion can be displayed; an identification-information generating portion that is provided on the insertion portions or the outer sleeve and issues insertion-portion identification information serving as identification information of each insertion portion; and an identification-information output unit that acquires the insertion-portion identification information issued from the identification-information generating portion every time the insertion portion passes through the through-hole and outputs the acquired information to the main unit, wherein the main unit includes a control unit that identifies the insertion portion passing through the outer sleeve on the basis of the insertion-portion identification information sent from the identification-information output unit and displays the insertion-portion unique information of the identified insertion portion on the display unit.

According to this aspect, the outer sleeve is attached to the biological subject, and one of the insertion portions supported by the medical device is passed through the through-hole of the outer sleeve so as to insert the insertion portion into the body cavity in a less invasive manner. In this way, the affected side in the body cavity in the biological subject can be treated or examined with a small burden on the biological subject.

In this case, every time one of the insertion portions passes through the through-hole in the outer sleeve, the insertion-portion identification information issued from the identification-information generating portion of the insertion portion or the outer sleeve is acquired by the identification-information output unit and sent to the main unit. Then, the control unit identifies the insertion portion inserted into the body cavity in the biological subject on the basis of the insertion-portion identification information and displays the insertion-portion unique information of the insertion portion on the display unit. Thus, every time the insertion portion of the medical device inserted into the body cavity in the biological subject is switched, the information of the insertion portion displayed on the display unit can readily switched in association therewith.

In the aspect described above, the identification-information output unit may include a light-source unit that emits light and a detection unit that detects, as the insertion-portion identification information, reflected light resulting from the light emitted from the light-source unit being radiated onto and reflected at the identification-information generating portion.

With such a configuration, the insertion-portion identification information of the insertion portion can be readily acquired with a simple configuration of the light source unit and the detection unit each time the insertion portion is passed through the through-hole.

In the aspect described above, the identification-information generating portion may include high-reflectance sections having high optical reflectance and low-reflectance sections having low optical reflectance, and each of the insertion portions may have a different combination of the high-reflectance sections and the low-reflectance sections.

With such a configuration, a plurality of insertion portions can be readily identified in accordance with the combination of the high-reflectance sections and the low-reflectance sections.

In the aspect described above, at least two of the identification-information output units may be further included, and the order in which the identification-information output units acquire and output to the main unit the insertion-portion identification information issued from the identification-information generating portion may differ between a time of insertion of the insertion portion into the through-hole and a time of removal of the insertion portion from the through-hole.

With such a configuration, for each identification-information output unit, by simply linking the insertion-portion identification information to be output to the main unit to determination information that enables the transmission source to be determined it is possible to readily determine whether the insertion portion has been inserted into the through-hole or whether the insertion portion has been removed from the through-hole in accordance with the order of the insertion-portion identification information input to the main unit from the identification-information output units.

In the aspect described above, the outer sleeve may include an outer-sleeve-information output unit that outputs outer-sleeve identification information serving as unique identification information to the main unit, and the control unit may superpose the insertion-portion unique information of the identified insertion portion and the outer-sleeve identification information sent from the outer-sleeve-information output unit and display the superposed information on the display unit.

With such a configuration, the outer-sleeve identification information of the outer sleeve and the insertion-portion unique information of the insertion portion passed through the outer sleeve and inserted into the body of the biological subject can be understood simultaneously on the display unit.

In the aspect described above, a plurality of the outer sleeves may be further included, and the control unit may link the outer-sleeve identification information of the outer sleeves with the insertion-portion unique information of the insertion portions passed through the outer sleeves and inserted into the body cavity in the biological subject and display the linked information on the display unit.

With such a configuration, even when a plurality of insertion portions are simultaneously inserted into the body cavity of the biological subject, the insertion portion being used can be linked with the information on the display unit and understood at a glance.

In the aspect described above, the medical device may be a image acquisition device that acquires an image of the inside of the body cavity in the biological subject with the insertion portions, and the control unit may display the image acquired by the identified insertion portion as the insertion-portion unique information on the display unit.

With such a configuration, an image of the affected site inside the body cavity in the biological subject acquired by an insertion portion is automatically displayed on the display unit when the insertion portion used by the image acquisition device is switched. Thus, the trouble of switching the insertion portion used and the image displayed on the display unit in association therewith can be avoided, and the body cavity in the biological subject can be efficiently examined with a desired insertion portion appropriate for the examination conditions.

In the aspect described above, the main unit may include a storage unit that stores the insertion-portion identification information sent from the identification-information output unit and an image recording unit that records an image acquired by the insertion portion, and the control unit may compare the insertion-portion identification information of a newly identified insertion portion with the insertion-portion identification information stored in the storage unit immediately before, record an image acquired by the newly identified insertion portion in the image recording unit if the insertion-portion identification information differs, and stop the recording performed by the image recording unit if the insertion-portion identification information matches.

With such a configuration, the image acquired by the insertion portion is recorded in the image recording unit so long as the same insertion portion of the image acquisition device is inserted into the body cavity in the biological subject, and the image recording performed by the image recording unit is stopped upon removal of the insertion portion from the body cavity in the biological subject. Thus, it is possible to efficiently record only desired images of the inside of the body cavity in the biological subject every time the insertion portion to be used is switched.

In the aspect described above, the insertion portions may include an illumination light source that emits illumination light for illuminating the inside of the body cavity in the biological subject; the main unit may include a storage unit that stores the insertion-portion identification information sent from the identification-information output unit; and the control unit may compare the insertion-portion identification information of a newly identified insertion portion with the insertion-portion identification information stored in the storage unit immediately before, turn on the illumination light source, or increase the brightness of the illumination light source, of the newly identified insertion portion if the insertion-portion identification information differs, and turn off the illumination light source, or decrease the brightness of the illumination light source, of the newly identified insertion portion if the insertion-portion identification information matches.

With such a configuration, the illumination light source is turned on or the brightness is increased while the insertion portion is inserted into the body cavity in the biological subject, whereas the illumination light source is turned off or the brightness is decreased upon removal of the insertion portion from the body cavity in the biological subject. In this way, the operating burden on the operator can be reduced while preventing his or her view from being blocked.

In the aspect described above, the main unit may include a storage unit that stores the insertion-portion identification information sent from the identification-information output unit; and the control unit may compare the insertion-portion identification information of a newly identified insertion portion with the insertion-portion identification information stored in the storage unit immediately before, increase the backlight brightness of the display unit if the insertion-portion identification information differs, and decrease the backlight brightness of the display unit if the insertion-portion identification information matches.

With such a configuration, the display unit is bright while the insertion portion is operated inside the body cavity in the biological subject, whereas the display unit becomes dark upon removal of the insertion portion from the body cavity in the biological subject. Thus, wasteful power consumption can be suppressed.

In the aspect described above, the main unit may include a storage unit that stores the insertion-portion identification information sent from the identification-information output unit; and the control unit may compare the insertion-portion identification information of a newly identified insertion portion with the insertion-portion identification information stored in the storage unit immediately before, display the insertion-portion unique information of the newly identified insertion portion on the display unit if the insertion-portion identification information differs, and not display the insertion-portion unique information on the display unit if the insertion-portion identification information matches.

With such a configuration, the display unit may automatically enter an energy saving mode when the insertion portions are not in use, allowing power to be saved.

Advantageous Effects of Invention

The present invention is advantageous in that every time the insertion portion of the image acquisition device or the medical device inserted into the body cavity in the biological subject is switched, the information of the insertion portion displayed on the display unit can be readily switched in association therewith.

BRIEF DESCRIPTION OF DRAWINGS

FIG. 37 is a configuration diagram illustrating, in outline, a sheath unit of the medical system in FIG. 35.

DESCRIPTION OF EMBODIMENTS

First Embodiment

A medical system according to a first embodiment of the present invention will be described below with reference to the drawings.

Figure 1:
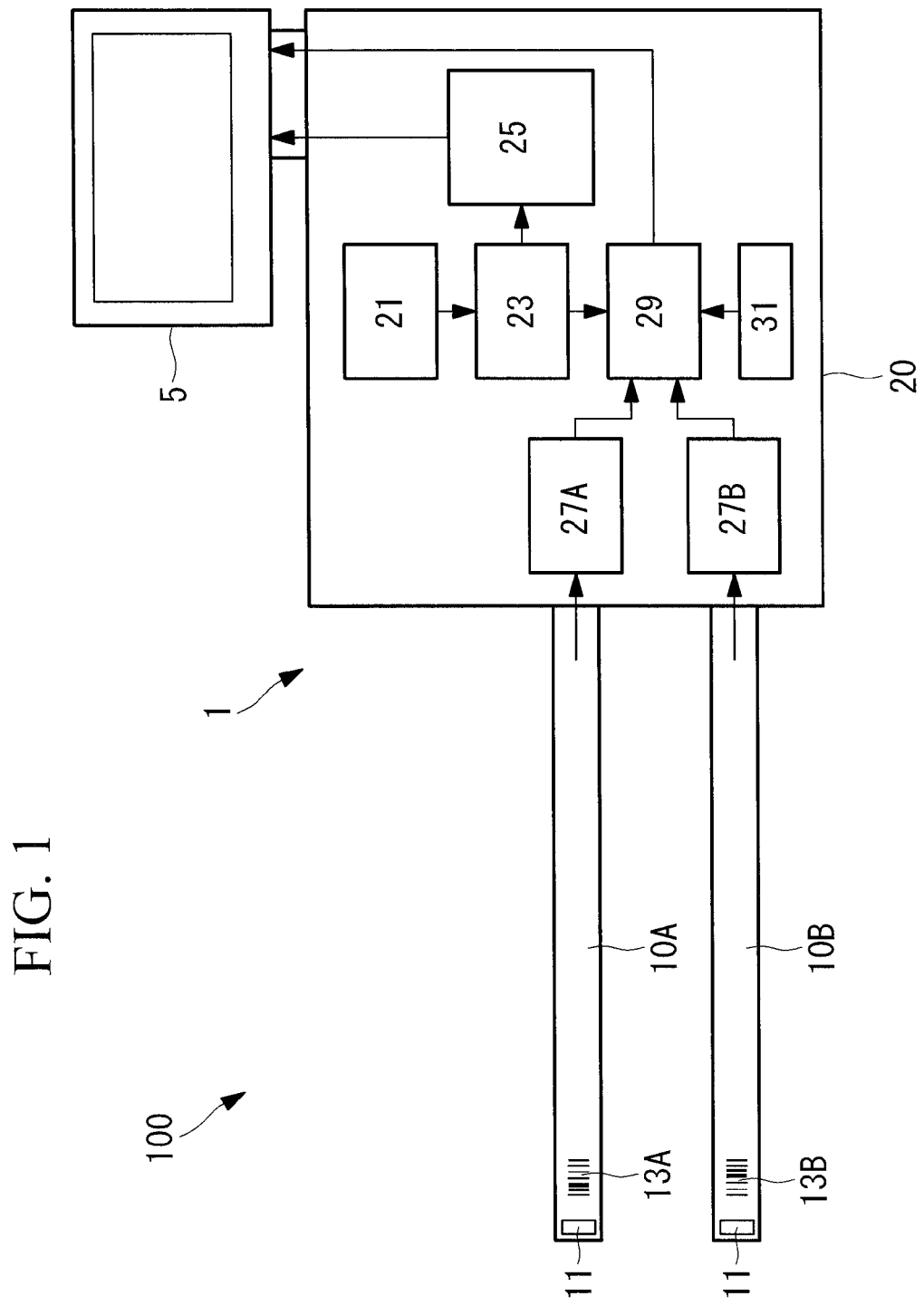
FIG. 1 is a configuration diagram illustrating, in outline, an endoscope device and a monitor of a medical system according to a first embodiment of the present invention.
Figure 2:
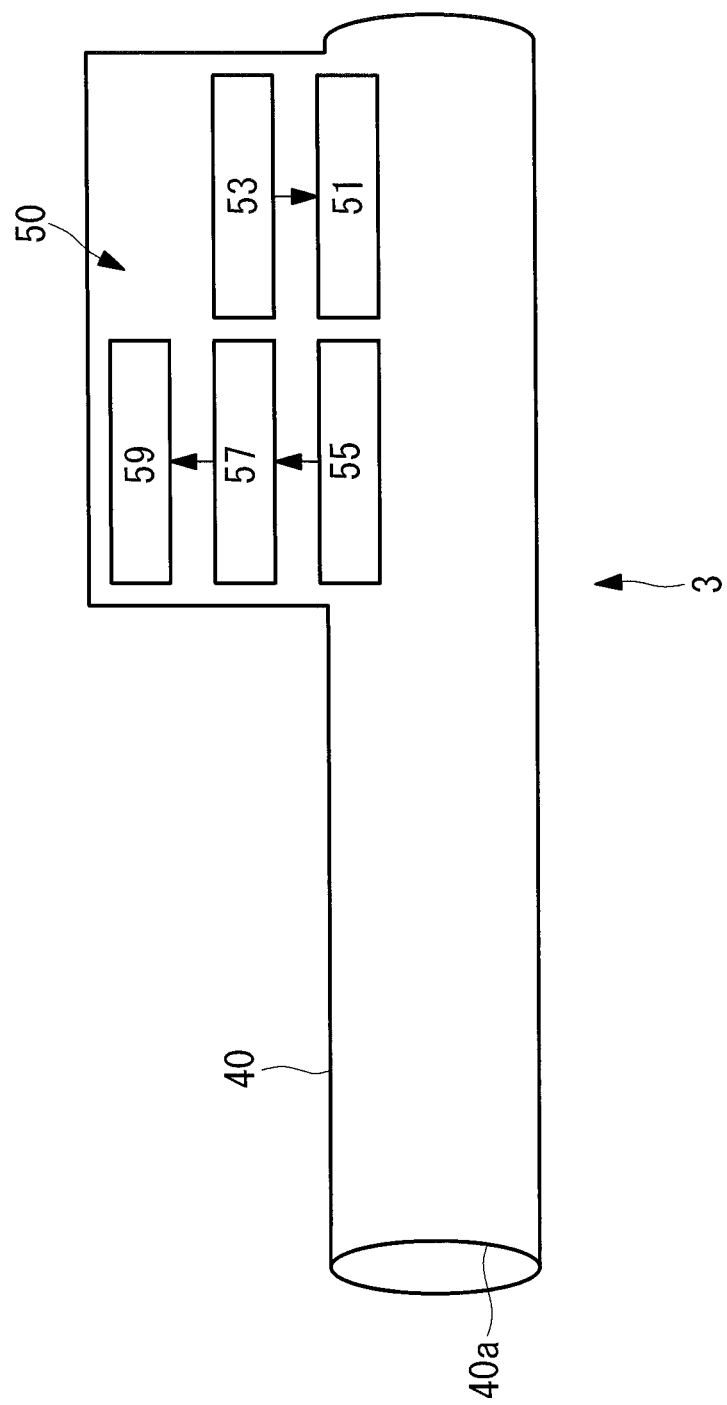
FIG. 2 is a configuration diagram illustrating, in outline, a sheath unit of the medical system according to the first embodiment of the present invention.

As illustrated in FIGS. 1 and 2, a medical system 100 according to this embodiment includes an endoscope device (medical device) 1 including a plurality of insertion portions 10A and 10B that are insertable into a body cavity in a biological subject; a sheath unit (outer sleeve) 3 that is attached to the biological subject and guides the insertion portion 10A or 10B of the endoscope device 1 into a body cavity in the biological subject; and a monitor (display unit) 5 that displays images, etc. acquired by the endoscope device 1.

The endoscope device 1 includes the two endoscope insertion portions 10A and 10B and a main unit 20 that supports the insertion portions 10A and 10B. The insertion portions 10A and 10B are long and substantially cylindrical and have bases that are fixed to or detachable from the main unit 20. The insertion portions 10A and 10B each include a CCD (image-acquisition element) 11 for acquiring images. Each CCD 11 is disposed at the tip of the insertion portions 10A or 10B and is capable of sending image-acquisition signals of the acquired images to the main unit 20.

The outer cylindrical surfaces near the tips of the insertion portions 10A and 10B have barcodes (identification-information generating portions) 13A and 13B that display identification information (insertion-portion identification information) unique to the insertion portions 10A and 10B. The barcodes 13A and 13B are composed of a plurality of high-reflectance sections that have high optical reflectance and a plurality of low-reflectance sections that have low reflectance, in different combinations for the insertion portions 10A and 10B and are constituted such that the plurality of high-reflectance sections and low-reflectance sections are arranged along the longitudinal directions of the insertion portions 10A and 10B.

The insertion portion 10A or 10B is selectively passed through the sheath unit 3 attached to the biological subject when inserted into the body cavity in the biological subject. The identification information of the barcode 13A or 13B is sent to the main unit 20 via the sheath unit 3 while the insertion portion 10A and 10B passes through the sheath unit 3.

As illustrated in FIG. 2, the sheath unit 3 includes a hollow tube-like sheath 40 that has a through-hole 40a through which the insertion portion 10A or 10B of the endoscope device 1 can be passed and an identification-signal generating unit (identification-information output unit) 50 that acquires the identification information of the insertion portion 10A or 10B that passes through the sheath 40 and outputs this to the main unit 20. The sheath unit 3 is attached to the biological subject by insertion of one end of the sheath 40 into an opening in the biological subject.

The identification-signal generating unit 50 is accommodated in the base of the sheath 40. The identification-signal generating unit 50 includes an LED light source (light source unit) 51 that emits infrared light toward the through-hole 40a of the sheath 40; an LED driver 53 that drives the LED light source 51; a photodiode (detection unit) 55 that detects the reflected light of infrared light emitted from the LED light source 51 and converts this to an electrical signal; a signal amplifying unit 57 that amplifies the electrical signal acquired by the photodiode 55; and a transmission antenna 59 that converts the amplified electrical signal to electromagnetic waves and transmits these to the main unit 20.

Upon passing the insertion portion 10A or the insertion portion 10B of the endoscope device 1 through the through-hole 40a of the sheath 40, the infrared light emitted from the LED light source 51 is radiated onto the barcode 13A of the insertion portion 10A (the barcode 13B in the case of the insertion portion 10B), and in response, the photodiode 55 can detect the reflected light reflected at the barcode 13A or 13B to acquire an electrical signal indicating the identification information of the insertion portion 10A or 10B. In this way, the identification information of the insertion portion 10A or 10B is sent to the main unit 20 via the signal amplifying unit 57 and the transmission antenna 59.

As illustrated in FIG. 1, the main unit 20 includes a reception antenna 21 that receives electromagnetic waves indicating the identification information of the insertion portion 10A or 10B sent from the transmission antenna 59 of the sheath unit 3 and converts these to an electrical signal; a signal converting unit 23 that performs level conversion and data string conversion of the electrical signal acquired by the reception antenna 21; and a power switching unit 25 that switches the ON/OFF state of the power supply of the monitor 5 on the basis of the electrical signal sent from the signal converting unit 23.

The main unit 20 includes image processing units 27A and 27B that convert the image acquisition signals sent from the CCDs 11 of the insertion portions 10A and 10B, respectively, to video signals (insertion-portion unique information); an image selector (control unit) 29 that selects one of the video signals acquired by the image processing units 27A and 27B on the basis of the identification information in the electrical signal sent from the signal converting unit 23 and causes the selected video signal to be displayed on the monitor 5; and a memory 31 that stores in advance the identification information of the insertion portions 10A and 10B as data arrays.

The operation of the medical system 100 having such a configuration will now be described.

Figure 3:
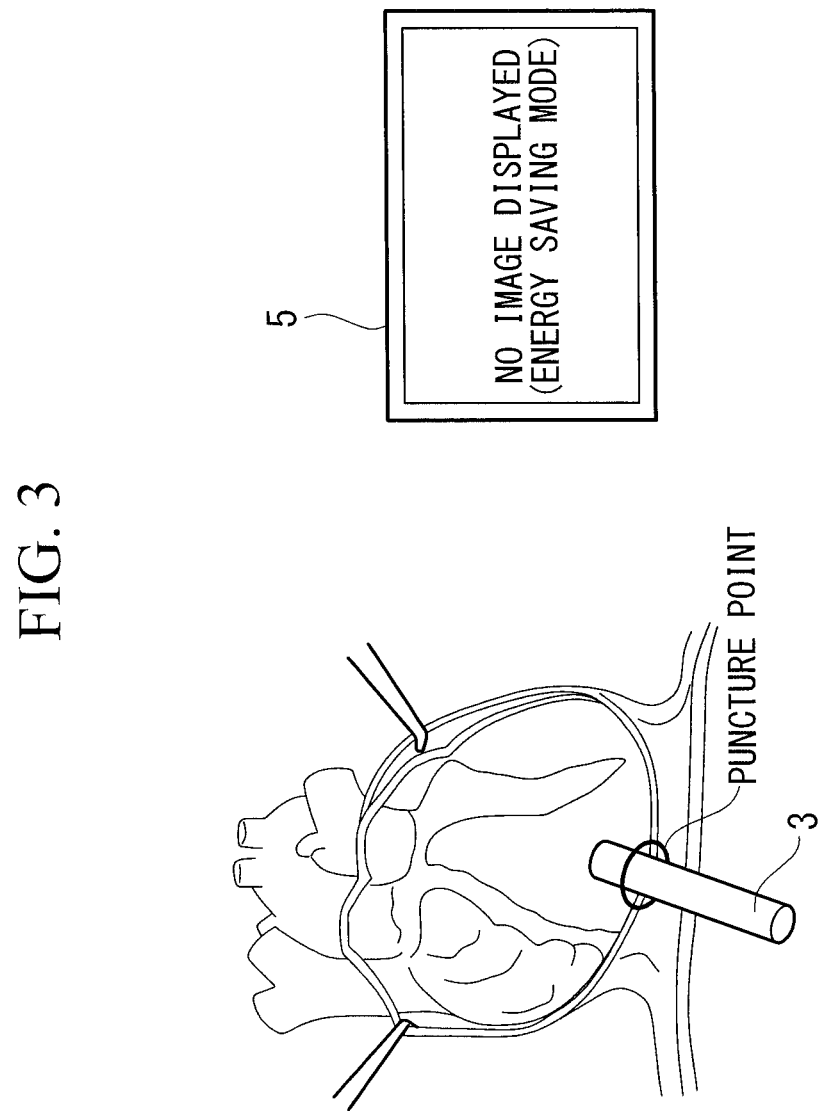
FIG. 3 is a diagram illustrating a state in which the sheath unit in FIG. 2 is attached to a biological subject and the display state of the monitor at that time.

To examine the inside of a body cavity in a biological subject with the medical system 100 according to this embodiment, first, as illustrated in FIG. 3, the tip of the sheath 40 of the sheath unit 3 is inserted into an incision in a biological subject S (a puncture point formed in the epicardium in FIG. 3), and the sheath unit 3 is attached to the biological subject S.

Infrared light is generated at the LED light source 51 of the identification-signal generating unit 50 in the sheath unit 3. In this state, each image is acquired by the CCD 11 of each of the insertion portions 10A and 10B, and the video signals are sent to the image selector 29 via the image processing units 27A and 27B, but an image is not displayed on the monitor 5.

Figure 4:
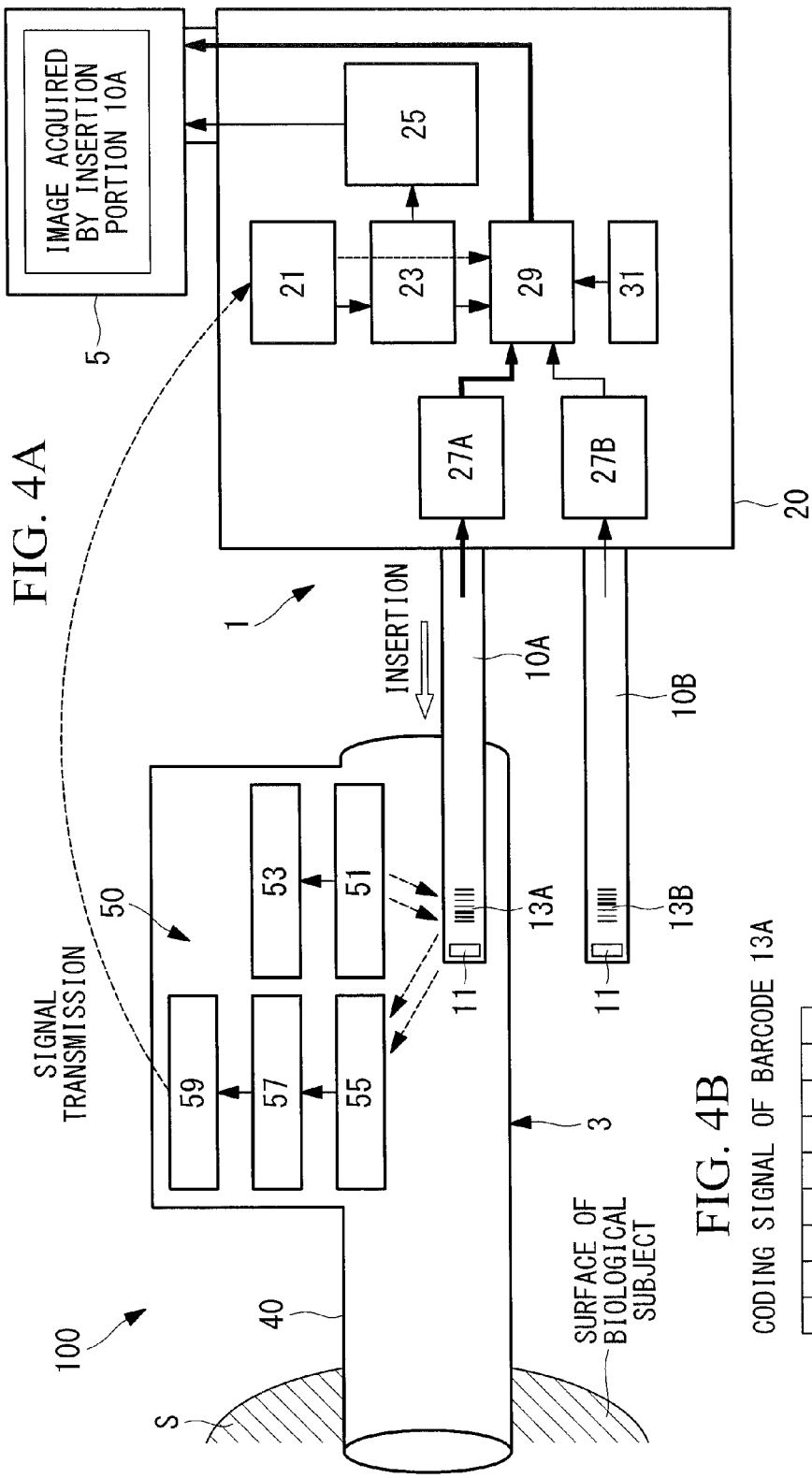
FIG. 4A is a diagram illustrating the insertion of one of the insertion portions into the sheath unit attached to the heart.
FIG. 4B is a diagram illustrating an example coding signal at the time of sheath insertion and an example coding signal at the time of sheath removal.

Then, one of the insertion portions 10A and 10B of the endoscope device 1 is passed through the sheath 40 of the sheath unit 3 and is inserted into the body cavity in the biological subject S. For example, as illustrated in FIG. 4A, upon insertion of the insertion portion 10A into the sheath unit 3, the barcode 13A of the insertion portion 10A passes through the light path of the infrared light emitted from the LED light source 51; as a result, the infrared light is radiated onto the barcode 13A, and the reflected light thereof is detected by the photodiode 55.

The reflected light detected by the photodiode 55 is converted to an electrical signal indicating the identification information of the barcode 13A. The electrical signal serves as a serial coding signal as a result of scanning the barcode with the infrared light. For example, as illustrated in FIG. 4B, the coding signal acquired during insertion of the insertion portion 10A into the sheath 40 is "101000110". The coding signal is amplified by the signal amplifying unit 57, is converted to electromagnetic waves by the transmission antenna 59, and is transmitted to the main unit 20.

The electromagnetic waves that have propagated through the air are received by the reception antenna 21 of the main unit 20, are converted to an electrical signal, which, after being subjected to level conversion and data string conversion by the signal converting unit 23, is input to the image selector 29 and the power switching unit 25. The image selector 29 checks for a match between the data array of the electrical signal indicating the identification information of the insertion portion 10A input from the signal converting unit 23 and the data arrays associated with the identification information of the insertion portions 10A and 10B stored in the memory 31.

Figure 5:
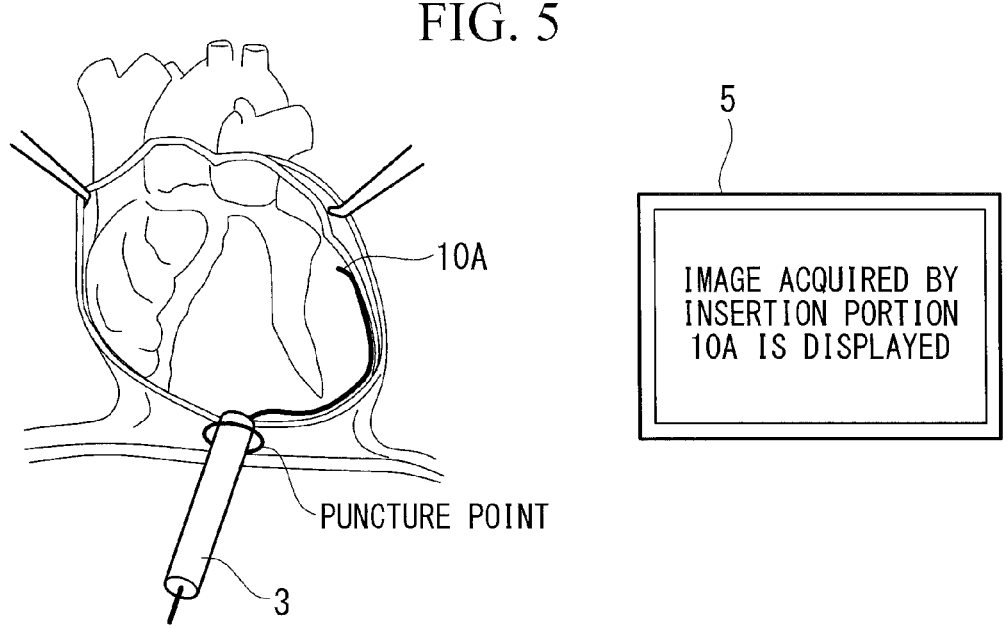
FIG. 5 is a diagram illustrating a state in which one of the insertion portions is inserted into the heart through the sheath unit and the display state of the monitor at that time.

In this case, the data arrays associated with the identification information of the insertion portion 10A match, and thus, the image selector 29 recognizes the insertion portion 10A as currently being in use (being inserted into the body cavity) and identifies the insertion portion 10A. Then, the image selector 29 selects the video signal sent from the image processing unit 27A and displays the image of the inside of the body cavity in the biological subject S acquired by the insertion portion 10A on the monitor 5, as illustrated in FIG. 5. In this way, the operator can examine the inside of the body cavity in the biological subject S while observing the image acquired by the insertion portion 10A on the monitor 5.

Subsequently, as the insertion portion 10A is removed from the sheath unit 3 after examination by the insertion portion 10A is completed, the barcode 13A passes through the light path of the infrared light from the LED light source 51. In such a case, since the scanning direction of the barcode 13A by the infrared light is opposite to that of the insertion, the coding signal acquired by converting the reflected light detected by the photodiode 55 is also opposite to that at the time of insertion. For example, as illustrated in FIG. 4B, the coding signal acquired during removal of the insertion portion 10A from the sheath 40 is "011000101".

Similar to insertion, the coding signal acquired by the photodiode 55 is received by the reception antenna 21 of the main unit 20 via the signal amplifying unit 57 and the transmission antenna 59 and is converted to an electrical signal, which is input to the image selector 29 and the power switching unit 25 via the signal converting unit 23. The electrical signal indicates removal of the insertion portion 10A.

Figure 6:
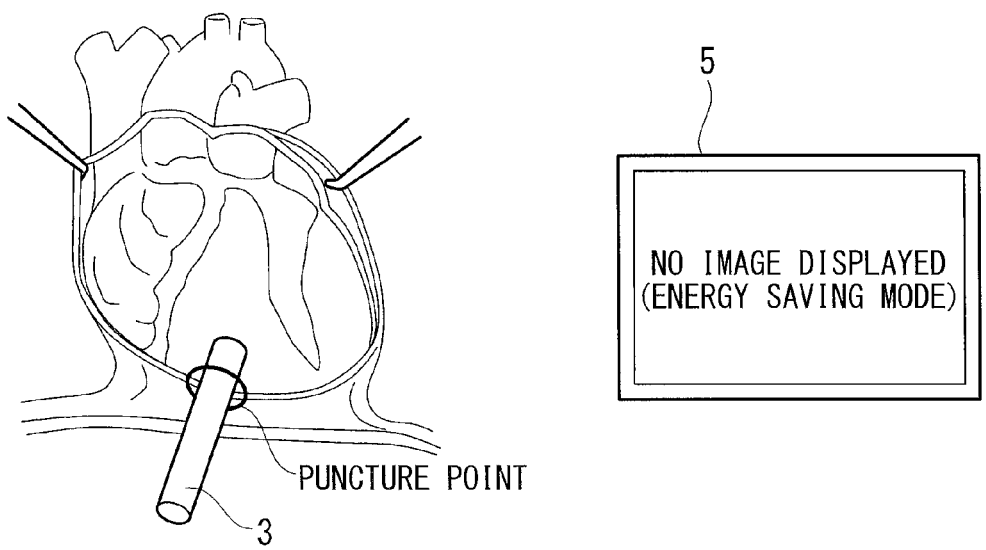
FIG. 6 is a diagram illustrating a state in which the insertion portion is removed from the heart and the sheath unit and the display state of the monitor at that time.

As illustrated in FIG. 6, the image selector 29 stops the output of the video signal to the monitor 5 in response to a trigger, which is the electrical signal, and the power supply of the monitor 5 is set to an energy saving mode by the power switching unit 25.

A case where the insertion portion 10B is inserted into the sheath unit 3 will now be described.

Figure 7:
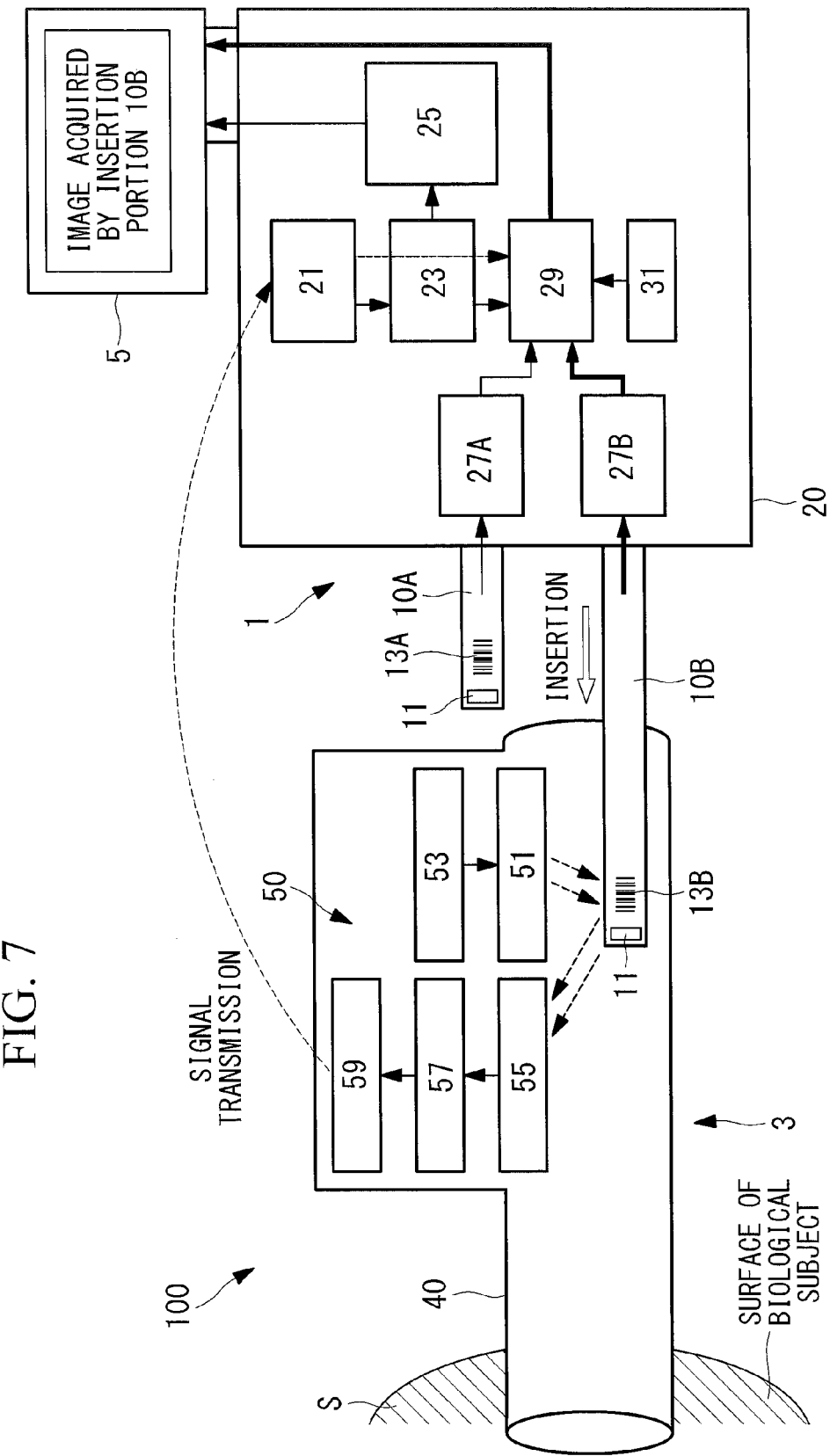
FIG. 7 is a diagram illustrating the insertion of the other insertion portion into the sheath unit attached to the heart.
Figure 8:
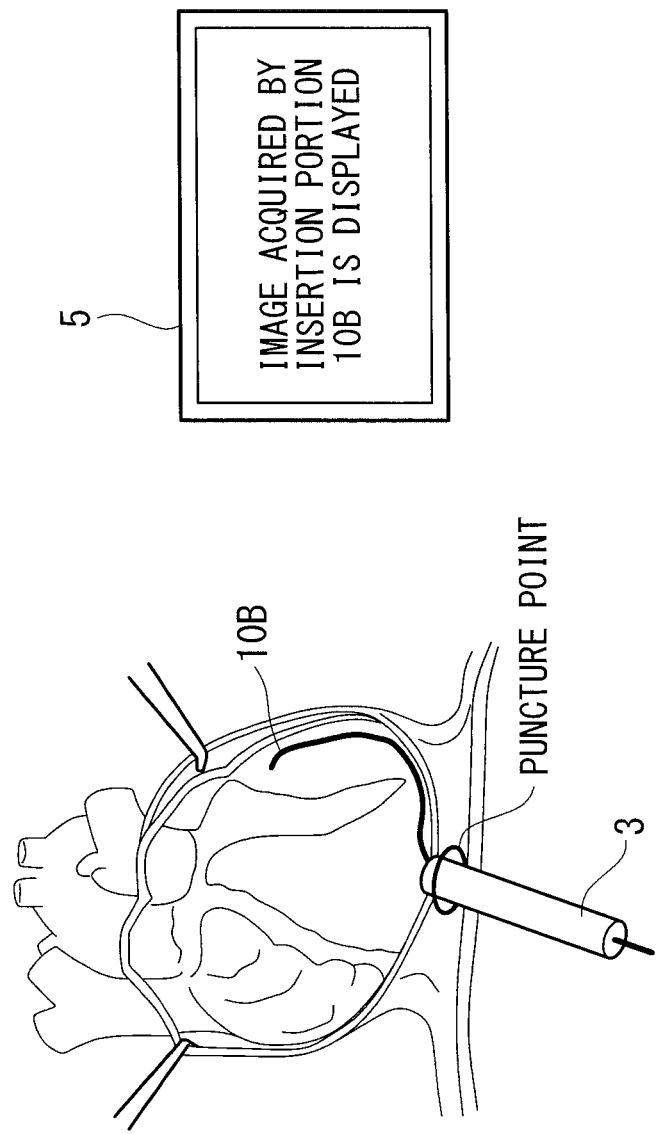
FIG. 8 is a diagram illustrating a state in which the other insertion portion is inserted into the heart through the sheath unit and the display state of the monitor at that time.

The basic operation of the case where the insertion portion 10B is inserted into the sheath unit 3 is the same as the case where the insertion portion 10A is inserted. As illustrated in FIG. 7, while the insertion portion 10B passes through the sheath 40 of the sheath unit 3, the image selector 29 recognizes the insertion portion 10B as currently being in use (being inserted into the body cavity), identifies the insertion portion 10B, and selects the video signal sent from the image processing unit 27B by identifying the insertion portion 10B. In this way, an image of the inside of the body cavity in the biological subject S acquired by the insertion portion 10B is displayed on the monitor 5, as illustrated in FIG. 8.

Similarly, as the insertion portion 10B is removed from the sheath unit 3, the image selector 29 stops the output of the video signal to the monitor 5 in response to a trigger, which is the electrical signal indicating removal of the insertion portion 10B acquired by the identification-signal generating unit 50, and the power supply of the monitor 5 is set to an energy saving mode by the power switching unit 25.

As described above, with the medical system 100 according to this embodiment, every time the plurality of insertion portions 10A and 10B of the endoscope device 1 inserted into the sheath unit 3 are switched, the unique identification information of the insertion portion 10A or 10B is acquired, and the insertion portion 10A or 10B currently in use is identified such that it is possible to readily switch between the images from the insertion portions 10A and 10B displayed on the monitor 5 in response to the switching of the insertion portions 10A and 10B inserted into the biological subject S.

In this way, the trouble of the operator having to switch the image displayed on the monitor 5 in accordance with the switching of the insertion portions 10A and 10B can be eliminated. Furthermore, power can be saved by automatically setting the monitor 5 to an energy saving mode when the insertion portions 10A and 10B are not in use.

The barcodes 13A and 13B are difficult to read if there is an encrustation of, for example, blood. Thus, in this embodiment, for example, a water repellent coating may be applied to the insertion portions 10A and 10B to prevent an encrustation forming on the barcodes 13A and 13B. Furthermore, for example, a sponge may be attached near the inlet of the through-hole 40a of the sheath 40 so that contamination on the surfaces of the insertion portions 10A and 10B is removed by the sponge when the insertion portions 10A and 10B are inserted into the sheath 40, which facilitates scanning.

This embodiment may be modified as described below.

Figure 9:
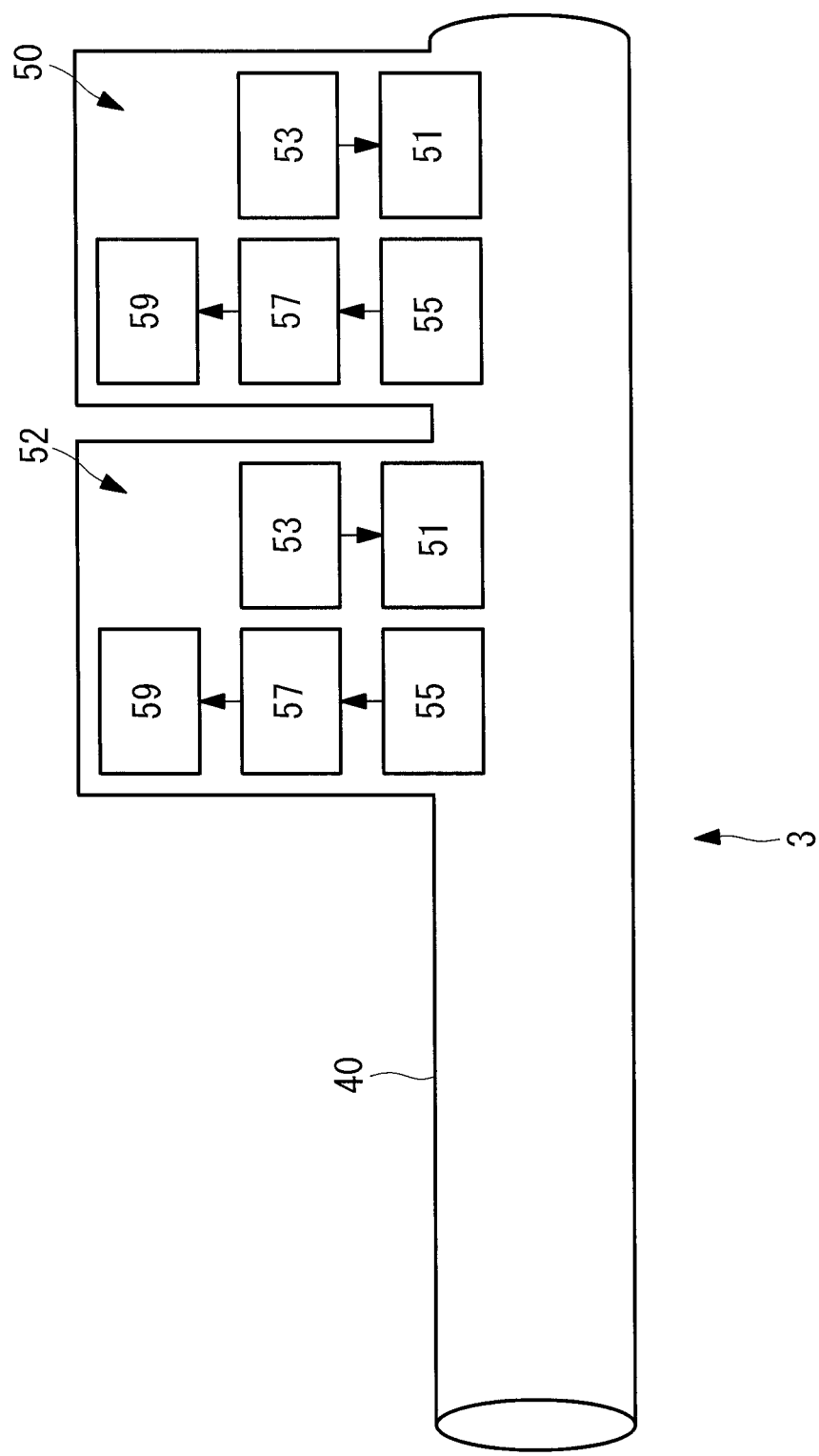
FIG. 9 is a diagram illustrating, in outline, a sheath unit of a medical system according to a modification of the first embodiment of the present invention.

In this embodiment, although a single identification-signal generating unit 50 is disposed at the base of the sheath 40, instead of this, as illustrated in FIG. 9, the sheath unit 3, for example, may include another identification-signal generating unit that is identical to the identification-signal generating unit 50. For example, the identification-signal generating unit 50 and an identification-signal generating unit 52 may be disposed a certain distance apart in the longitudinal direction of the sheath 40. The identification-signal generating unit 50 and the identification-signal generating unit 52 are disposed in this order from the inlet side of the sheath unit 3.

Figure 10:
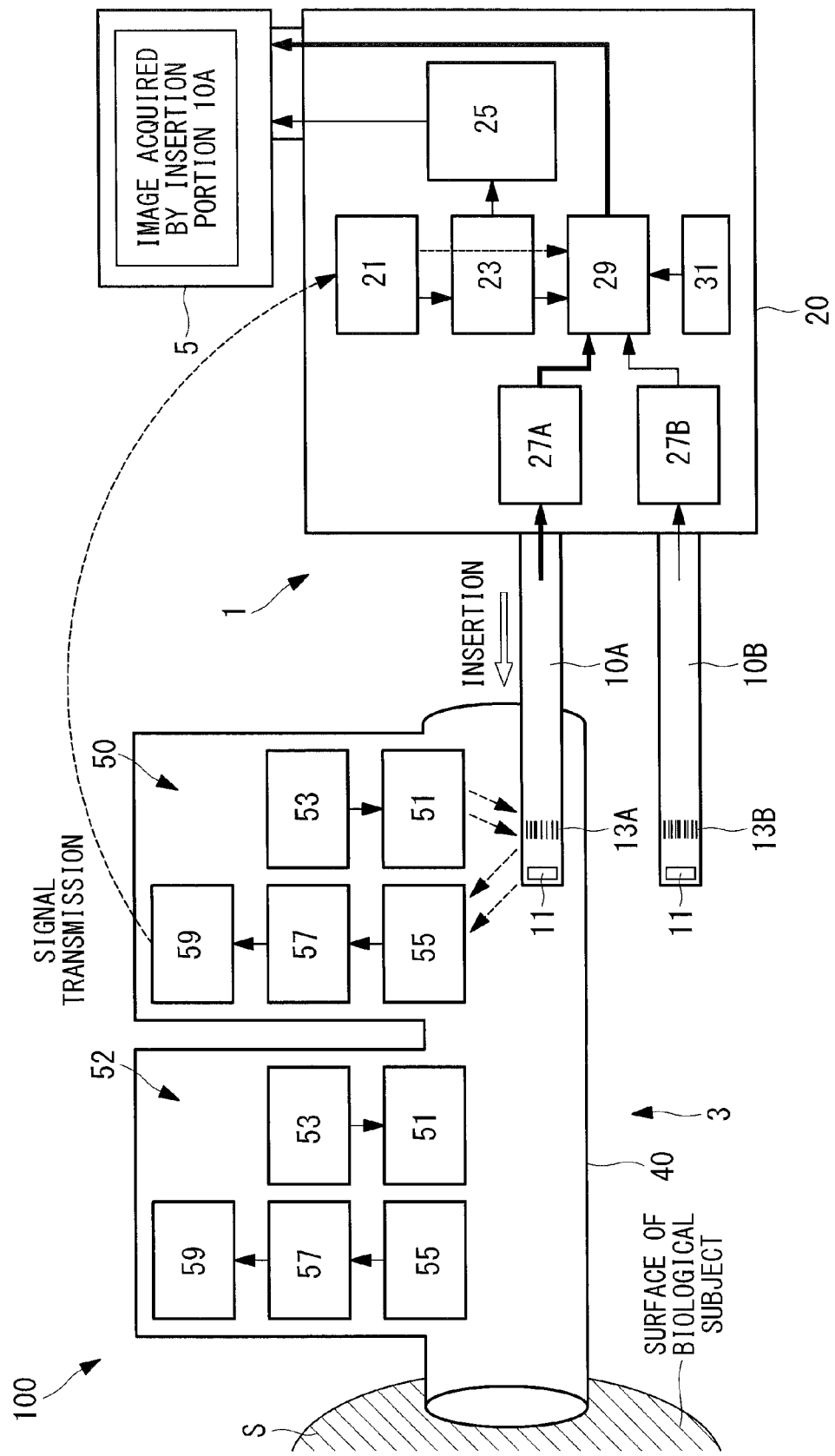
FIG. 10 is a diagram illustrating the insertion of one of the insertion portions into the sheath unit, illustrated in FIG. 9, attached to the heart.

In such a case, as illustrated in FIG. 10, as the insertion portion 10A is inserted into the sheath 40 of the sheath unit 3, the barcode 13A passes by the identification-signal generating unit 50 and the identification-signal generating unit 52, in this order. Then, electrical signals serving as identification information of the barcode 13A, which is acquired as a result of infrared light being radiated from the LED light source 51 and detected as reflected infrared light by the photodiode 55, are also generated at the identification-signal generating unit 50 followed by the identification-signal generating unit 52, and are sent in this order to the signal amplifying unit 57, the transmission antenna 59, the reception antenna 21, the signal converting unit 23, the image selector 29, and the power switching unit 25.

Figure 11:
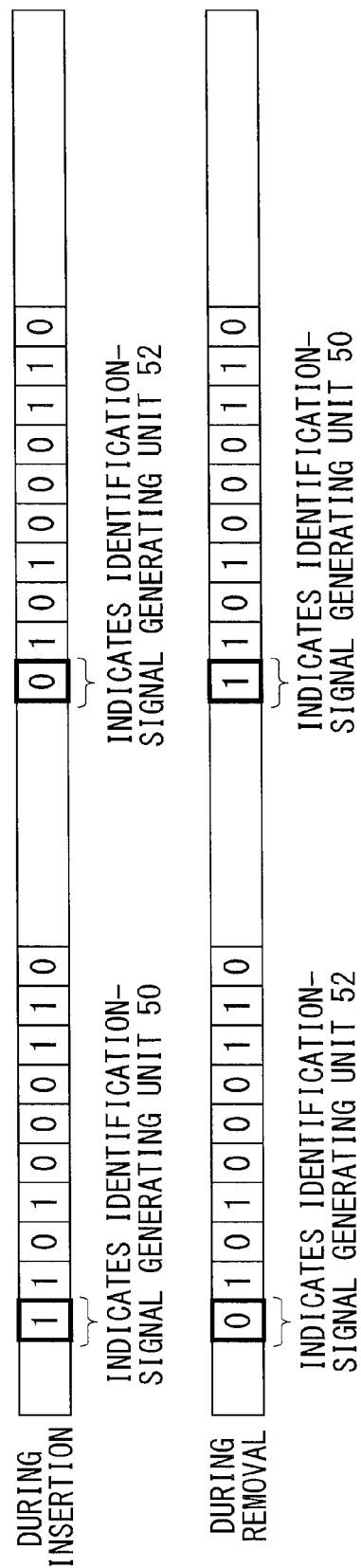
FIG. 11 is a diagram illustrating an example coding signal indicating identification information of the insertion portion acquired by each identification-signal generating unit.

In such a case, it is desirable to assign the higher order bit of the coding signal indicating the identification information of the insertion portion 10A acquired at each of the identification-signal generating units 50 and 52 as a transmission-source determining signal, as illustrated in FIG. 11, so as to identify the signal as the electrical signal serving as the identification information sent from the identification-signal generating unit 50 or the electrical signal serving as the identification information sent from the identification-signal generating unit 52. In this way, whether the insertion operation has been performed or the removal operation has been performed is readily determined on the basis of the order of the higher order bits input to the image selector 29 in chronological order (for example, 1 to 0 or 0 to 1).

According to this modification, the sequential reading of each of the barcodes 13A and 13B by the two identification-signal generating units 50 and 52 facilitates determination of the insertion operation and the removal operation of the insertion portions 10A and 10B, regardless of the shape of the barcodes 13A and 13B. For example, in this embodiment described above, determination of the operation at the time of insertion and the operation at the time of removal requires serial reading of the barcodes 13A and 13B; thus, there is a limitation in that the barcodes 13A and 13B must be aligned in the longitudinal direction of the insertion portions 10A and 10B (must be arranged in consideration of the scanning direction and must be one-dimensional symbols). Compared with this, according to this modification, since no relationship is established between the shape of the symbols and the determination of the operation at the time of insertion and removal, various shapes, such as two-dimensional symbols and matrix symbols of any shape can be freely selected as the barcodes 13A and 13B.

Second Embodiment

A medical system according to a second embodiment of the present invention will now be described.

Figure 12:
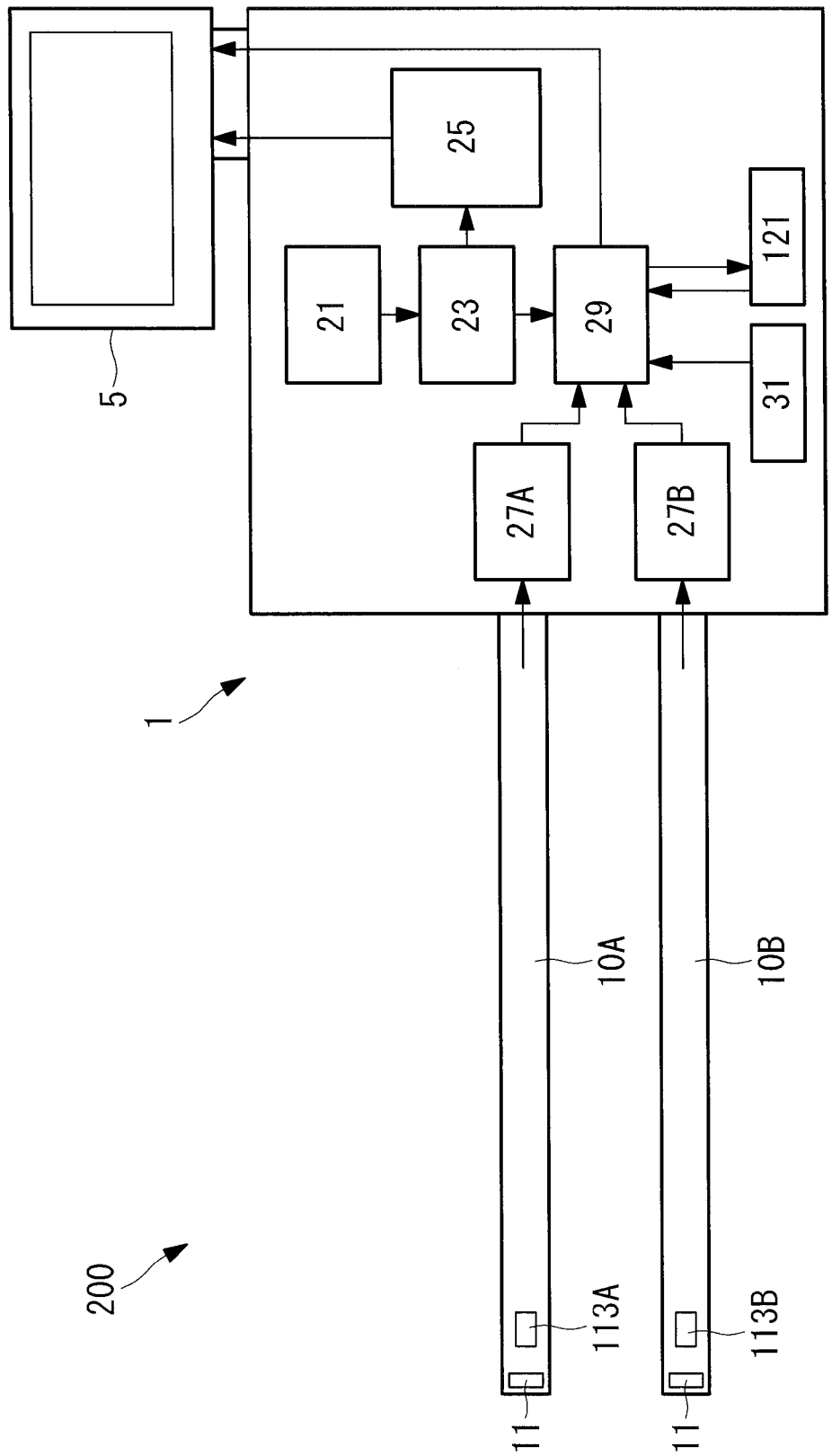
FIG. 12 is a configuration diagram illustrating, in outline, an endoscope device and a monitor of a medical system according to a second embodiment of the present invention.

As illustrated in FIG. 12, a medical system 200 according to this embodiment differs from the first embodiment in that the insertion portions 10A and 10B are respectively provided with RFID (radio frequency identification) tags 113A and 113B that are capable of outputting unique identification information (insertion-portion identification information) instead of the barcodes 13A and 13B.

Hereinafter, components that have the same configuration as those in the medical system 100 according to the first embodiment are designated by the same reference numerals, and descriptions thereof are omitted.

Figure 13:
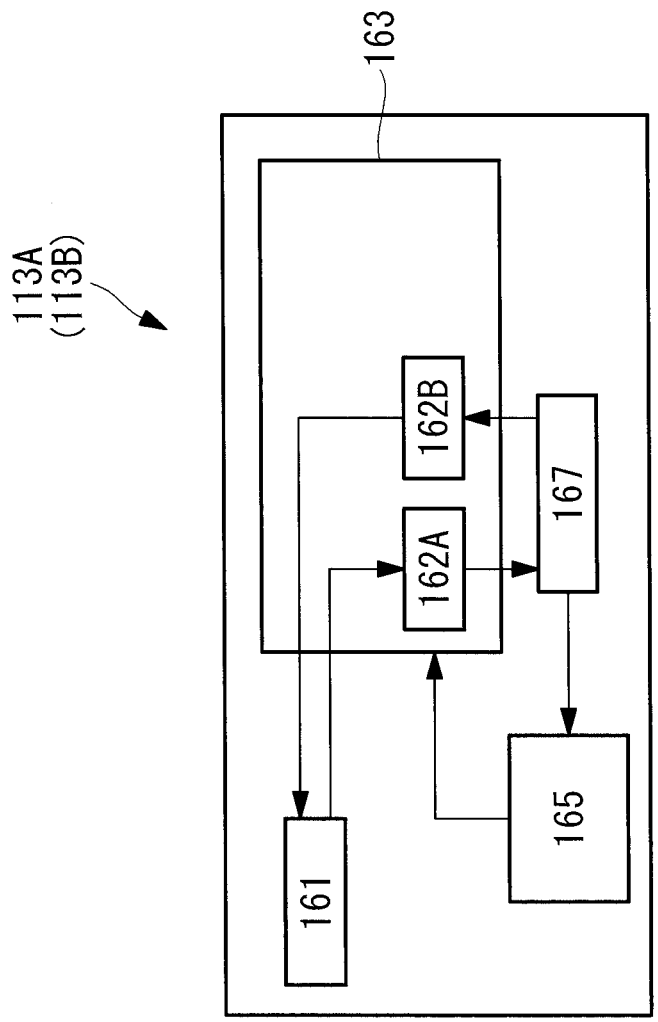
FIG. 13 is a configuration diagram illustrating, in outline, an RFID tag of an insertion portion in FIG. 12.

The RFID tags 113A and 113B are embedded in the tips of the insertion portions 10A and 10B, respectively. As illustrated in FIG. 13, the RFID tags 113A and 113B each include a memory 161 that stores identification information of the insertion portion 10A or 10B; a control unit 163 that has a D/A converting unit 162A that performs encoding of the content of the communication and an A/D converting unit 162B that performs decoding; a power supply unit 165 that drives the control unit 163; and an antenna 167 that supplies electric power to the power supply unit 165 and functions as a transmission/reception antenna for transmitting and receiving carrier waves.

Figure 14:
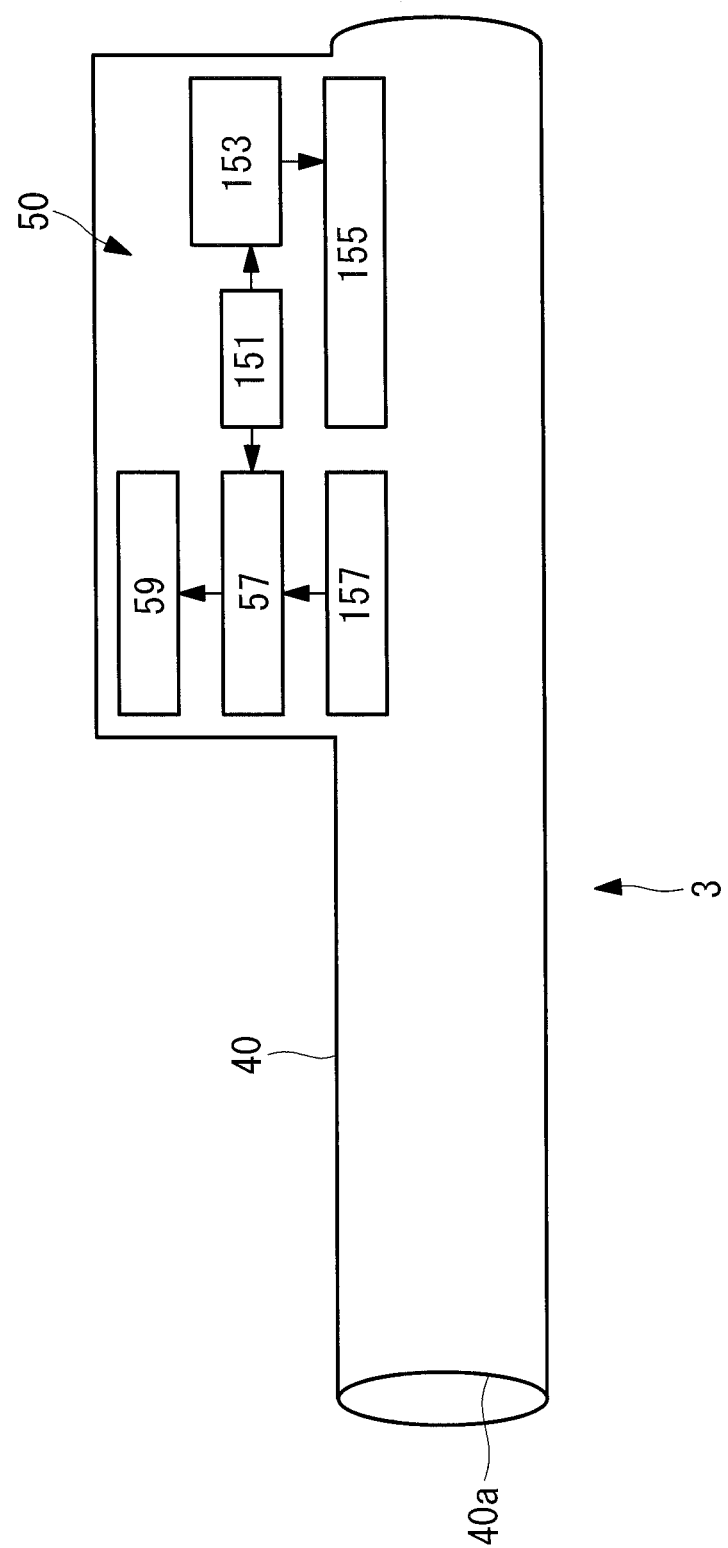
FIG. 14 is a configuration diagram illustrating, in outline, a sheath unit of the medical system according to the second embodiment of the present invention.

As illustrated in FIG. 14, instead of the LED light source (light source unit) 51, the LED driver 53, and the photodiode (detection unit) 55, the identification-signal generating unit 50 includes a power supply unit 151 that generates electrical power; a control-signal generating unit 153 that generates control signals for controlling the RFID tags 113A and 113B of the insertion portions 10A and 10B using the electrical power from the power supply unit 151; a transmission/power-transmission antenna 155 that transmits electromagnetic waves including the control signals inside the through-hole 40a of the sheath 40; and a reception antenna 157 that receives the carrier waves from the RFID tags 113A and 113B and converts these to electrical signals. The identification-signal generating unit 50 amplifies the electrical signals acquired by the reception antenna 157 at the signal amplifying unit 57, converts the electrical signals amplified by the signal amplifying unit 57 to electromagnetic waves by the transmission antenna 59, and transmits these to the main unit 20.

The main unit 20 includes a memory (storage unit) 121 that temporality stores the data arrays of the identification information input from the signal converting unit 23 by the image selector 29. Upon input of the electrical signal of the identification information input from the signal converting unit 23, the image selector 29 determines whether the data array of the electrical signal matches the data arrays of the identification information stored in the memory 121.

The operation of the medical system 200 having such a configuration will now be described.

Examination of the inside of a body cavity in a biological subject using the medical system 200 according to this embodiment is achieved by attaching the sheath unit 3 to the biological subject and emitting electromagnetic waves containing a control signal from the transmission/power-transmission antenna 155 of the identification-signal generating unit 50.

Figure 15:
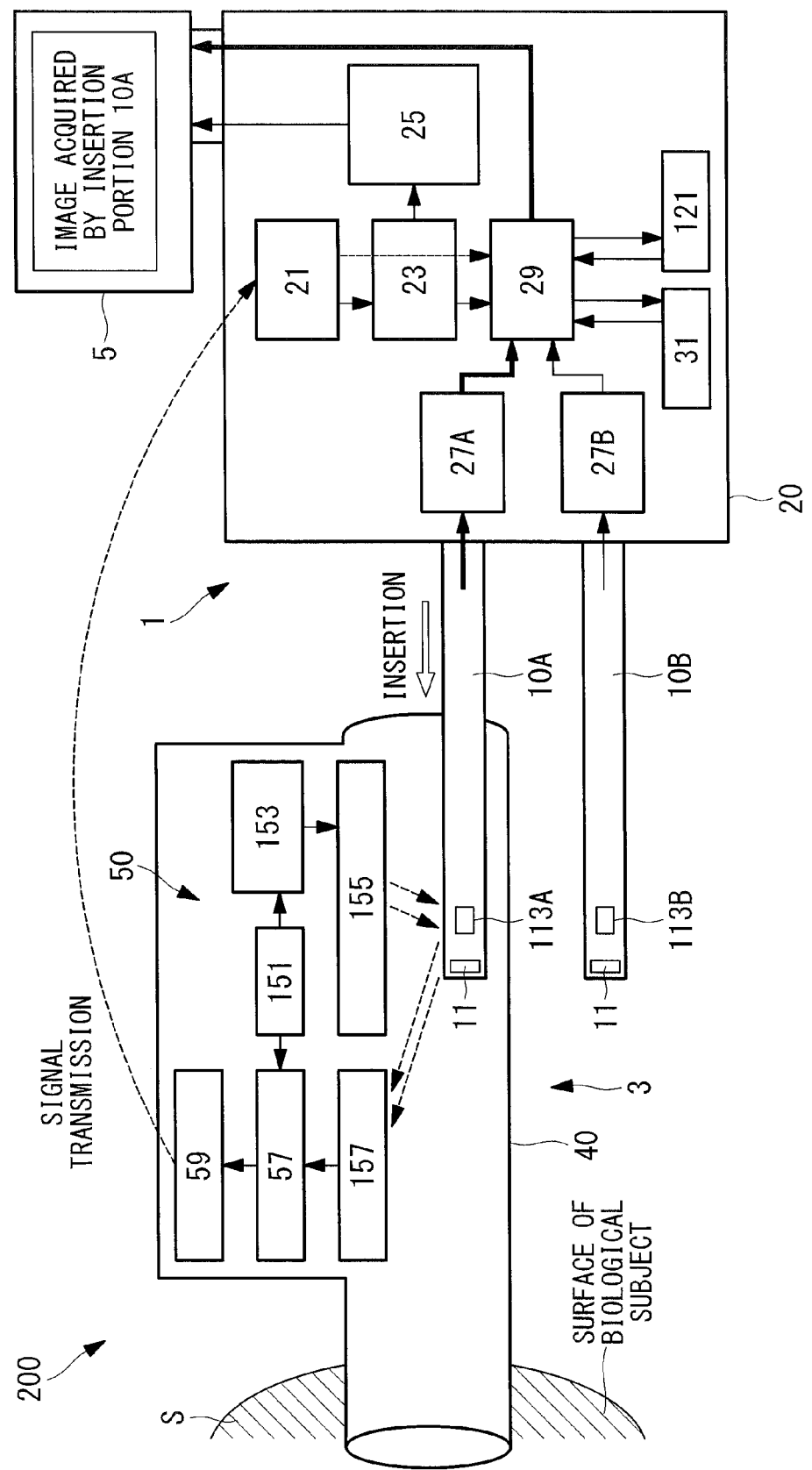
FIG. 15 is a diagram illustrating the insertion of one of the insertion portions into the sheath unit, illustrated in FIG. 14, attached to the heart.

Upon insertion of the insertion portion 10A into the sheath 40 of the sheath unit 3, as illustrated in FIG. 15, the RFID tag 113A passes through the electromagnetic waves emitted from the transmission/power-transmission antenna 155 so that the antenna 167 of the RFID tag 113A receives the electromagnetic waves. The antenna 167 generates an electromotive force by a resonance effect (electromagnetic induction) in response to the reception of the electromagnetic waves. The generated electromotive force is transmitted to the power supply unit 165, and the power supply unit 165 generates power to drive the control unit 163. A part of the electromotive force contains the control signal. The control signal is input to the A/D converting unit 162B of the control unit 163.

The A/D converting unit 162B decodes the control signal sent from the antenna 167 and transmits it to the memory 161. The electrical signal of the identification information stored in the memory 161 is transmitted to the control unit 163 on the basis of the input control signal. In the control unit 163, the electrical signal is encoded and modulated into carrier waves by the D/A converting unit 162A and is sent to the antenna 167.

The antenna 167 transmits the carrier waves to the inside of the sheath 40, and the reception antenna 157 of the identification-signal generating unit 50 receives the carrier waves and converts them to an electrical signal. The electrical signal is amplified by the signal amplifying unit 57, is input to the transmission antenna 59, and is converted to electromagnetic waves, which are transmitted to the main unit 20.

The electromagnetic waves that have propagated through the air are received by the reception antenna 21 of the main unit 20 and are converted to an electrical signal, which is input to the signal converting unit 23. The signal converting unit 23 performs level conversion and data string conversion on the electrical signal and transmits this to the image selector 29 and the power switching unit 25.

In the image selector 29, the electrical signal transmitted from the signal converting unit 23 is temporarily stored in the memory 121, and it is checked whether there is a match between the data array of the electrical signal and the data arrays of the identification information stored in the memory 31. In this case, the image selector 29 recognizes the insertion portion 10A as currently being in use (inserted in the body) since, as a result of the match checking, a match is found with the data arrays of the identification information in the memory 31. Then, the image selector 29 identifies the insertion portion 10A, selects the video signal sent from the image processing unit 27A, and displays the image of the inside of the body cavity in the biological subject S acquired by the insertion portion 10A on the monitor 5.

Subsequently, removal of the insertion portion 10A from the sheath unit 3 results in the input of an electrical signal of identification information that is identical to that at the time of insertion to the image selector 29 and the power switching unit 25. In such a case, as a result of the image selector 29 and the power switching unit 25 determining that data arrays of the same electrical signal have been input two consecutive times, the image selector 29 stops the transmission of the video signal to the monitor 5, and the power switching unit 25 sets the power supply of the monitor 5 to an energy saving mode.

The procedure for determining that identical data arrays have been input two consecutive times will be described with reference to the flow chart in FIG. 16.

Figure 16:
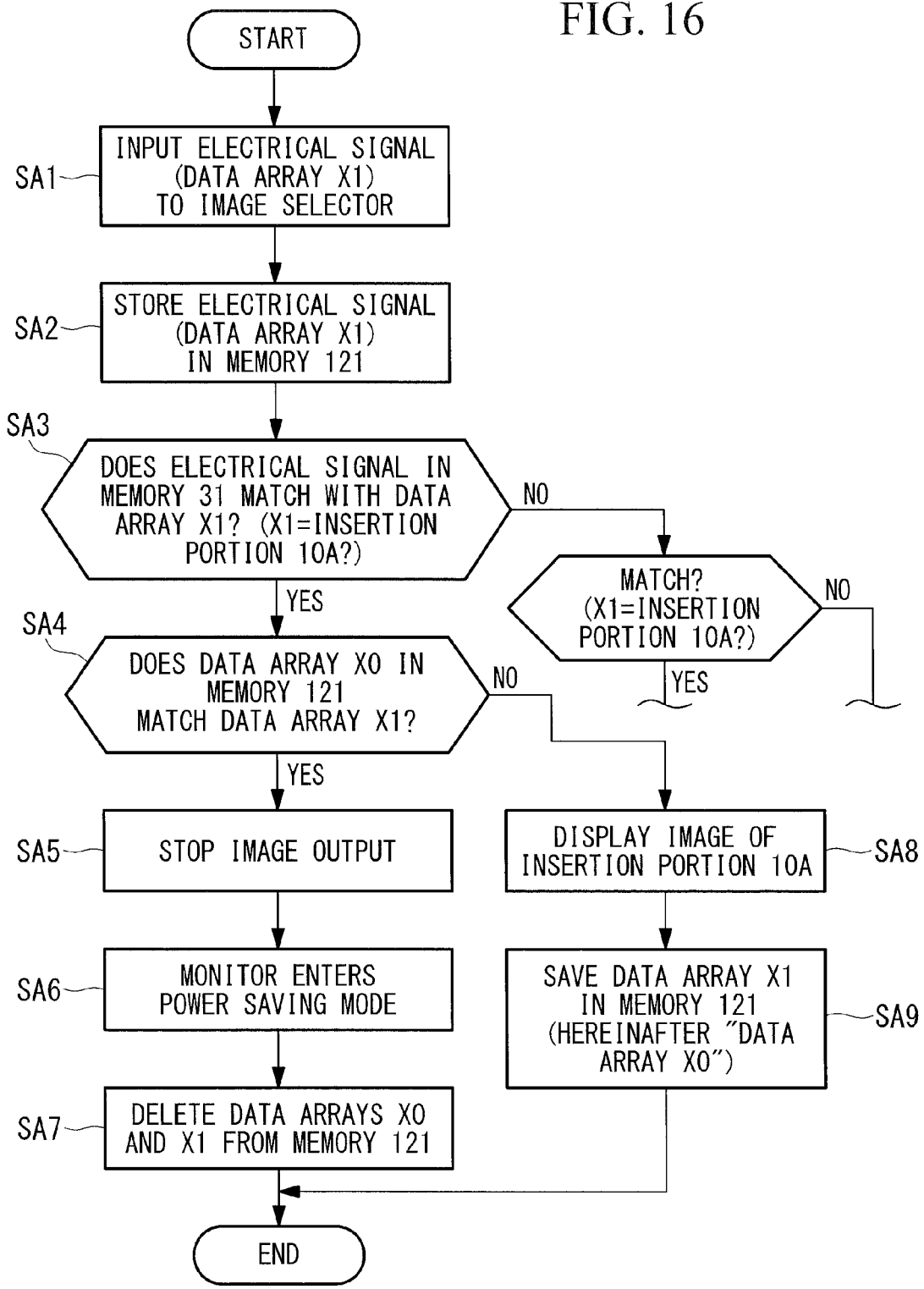
FIG. 16 is a flow chart for explaining examination of the heart with the medical system according to the second embodiment of the present invention.

Referring to FIG. 16, X0 represents the preceding data array of the identification information stored in the memory 121, and X1 represents the subsequent data array. When an electrical signal (data array X1) indicating the identification information of the insertion portion 10A or 10B is input to the image selector 29 (Step SA1), the data array X1 of the electrical signal is temporarily stored in the memory 121 (Step SA2).

The image selector 29 first checks for a match between the data array X1 of a new electrical signal and the data arrays of the identification information of the insertion portion 10A or 10B stored in the memory 31 (Step SA3). If, as a result of match checking, the data arrays match, then the image selector 29 checks for a match between the subsequent data array X1 of the electrical signal and the preceding data array X0 stored in the memory 121 (Step SA4).

If the result of match checking in Step SA4 indicates a match, the image selector 29 stops the transmission of the video signal from the insertion portion 10A corresponding to the identification information of the subsequent data array X1 (Step SA5). Furthermore, the power switching unit 25 sets the power supply of the monitor 5 to an energy saving mode (Step SA6). Furthermore, the image selector 29 deletes all data to reset the memory 121 (Step SA7).

Figure 17:
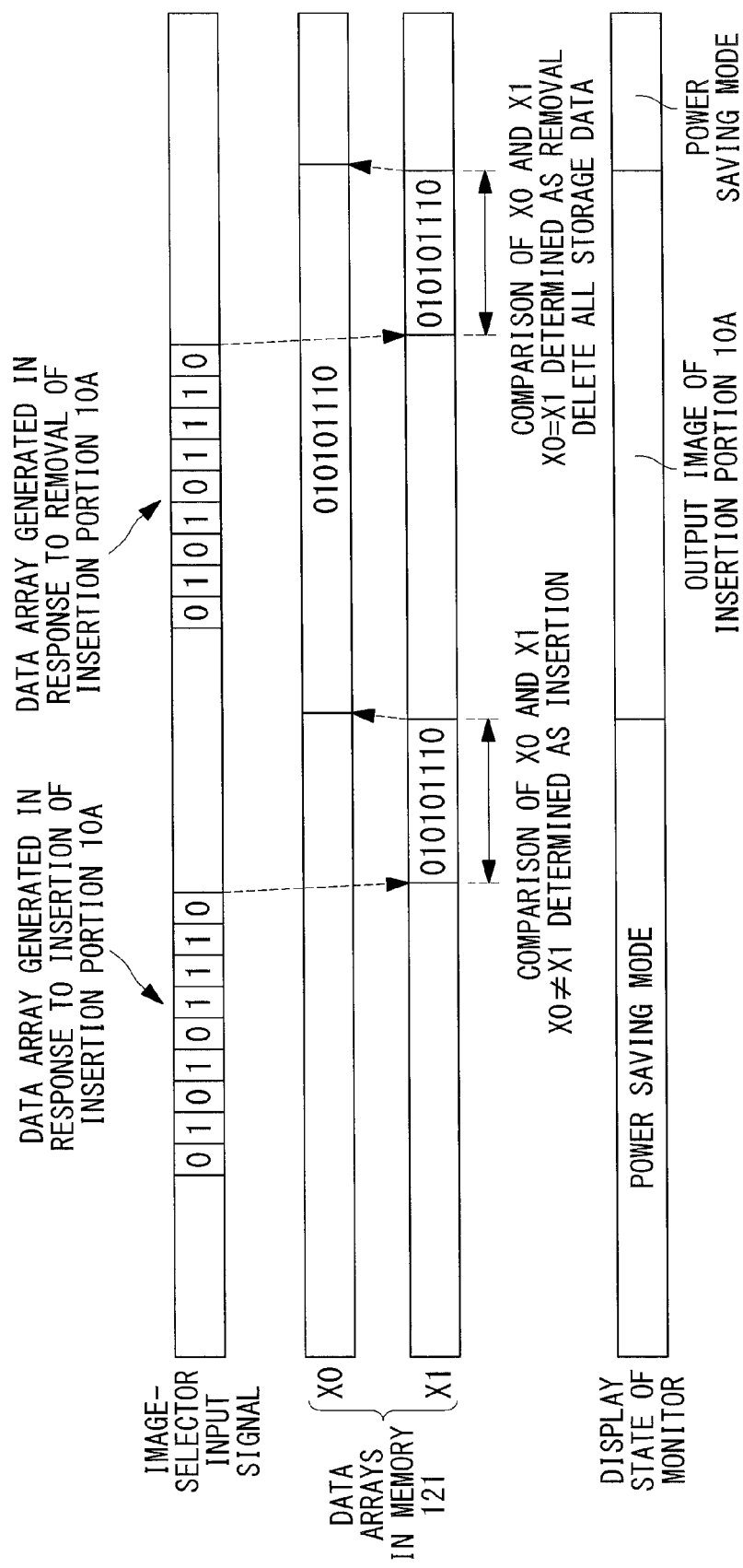
FIG. 17 is a diagram illustrating the relationship among the data array of an electrical signal of the identification information input to an image selector, a preceding data array and a subsequent data array of identification information stored in a memory, and the display state of the monitor.

Meanwhile, if the result of match checking in Step SA4 does not indicate a match, the video signal from the insertion portion 10A serving as the identification information of the data array X1 is displayed on the monitor 5 (Step SA8). Then, the subsequent data array X1 of the identification information newly stored in the memory 121 overwrites the preceding data array X0 and is saved as a preceding data array X0 (Step SA9). FIG. 17 illustrates the relationship between a data array of an electrical signal of identification information input to the image selector 29, and a preceding data array X0 and a subsequent data array X1 of the identification information stored in the memory 121.

Figure 18:
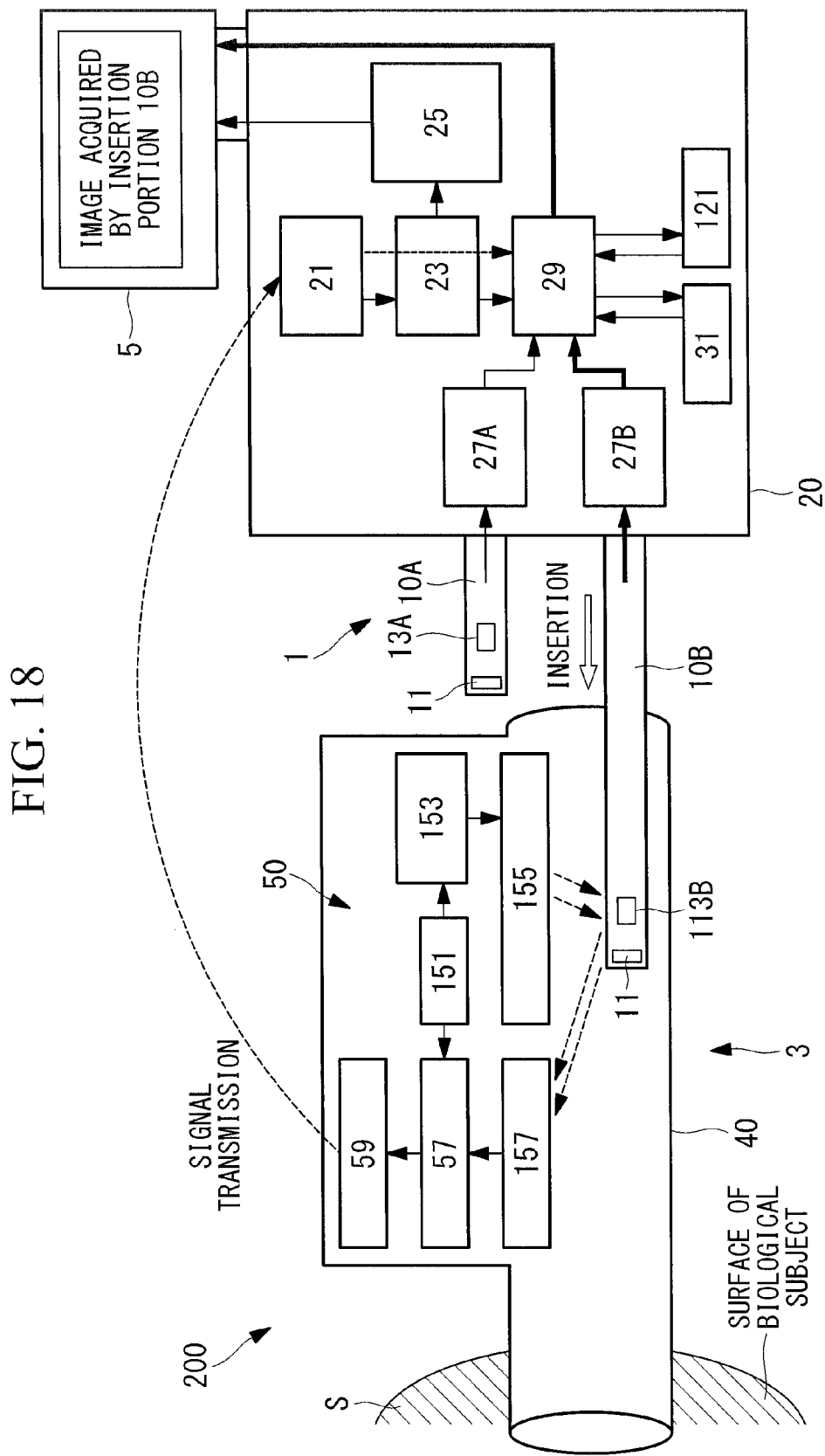
FIG. 18 is a diagram illustrating the insertion of the other insertion portion into the sheath unit, illustrated in FIG. 12, attached to the heart.

As illustrated in FIG. 18, the basic operation of a case where the insertion portion 10B is inserted into the sheath unit 3 is the same as a case where the insertion portion 10A is inserted. As the insertion portion 10B passes through the sheath 40 of the sheath unit 3, the image selector 29 recognizes the insertion portion 10B as currently being in use (being inserted into the body cavity), identifies the insertion portion 10B, and selects the video signal sent from the image processing unit 27B. In this way, an image of the inside of the body cavity in the biological subject S acquired by the insertion portion 10B is displayed on the monitor 5.

As described above, the medical system 200 according to this embodiment uses the RFID tags 113A and 113B to assure the acquisition of identification information and identify the insertion portions 10A and 10B passing through the sheath unit 3 regardless of the encrustation of blood, etc. on the insertion portions 10A and 10B.

Third Embodiment

A medical system according to a third embodiment of the present invention will now be described.

Figure 19:
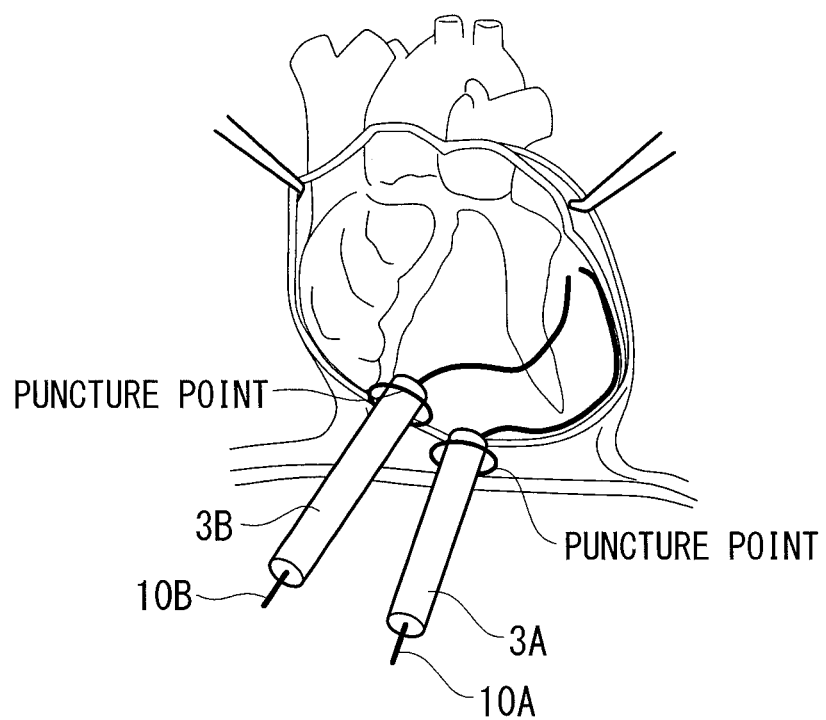
FIG. 19 is a diagram illustrating, in outline, an insertion portion of a medical system according to a third embodiment of the present invention.

As illustrated in FIG. 19, a medical system 300 according to this embodiment differs from those according to the first and second embodiments in that two sheath units 3A and 3B are provided.

Hereinafter, components that have the same configuration as those in the medical systems 100 and 200 according to the first and second embodiments are designated by the same reference numerals, and descriptions thereof are omitted.

Figure 20:
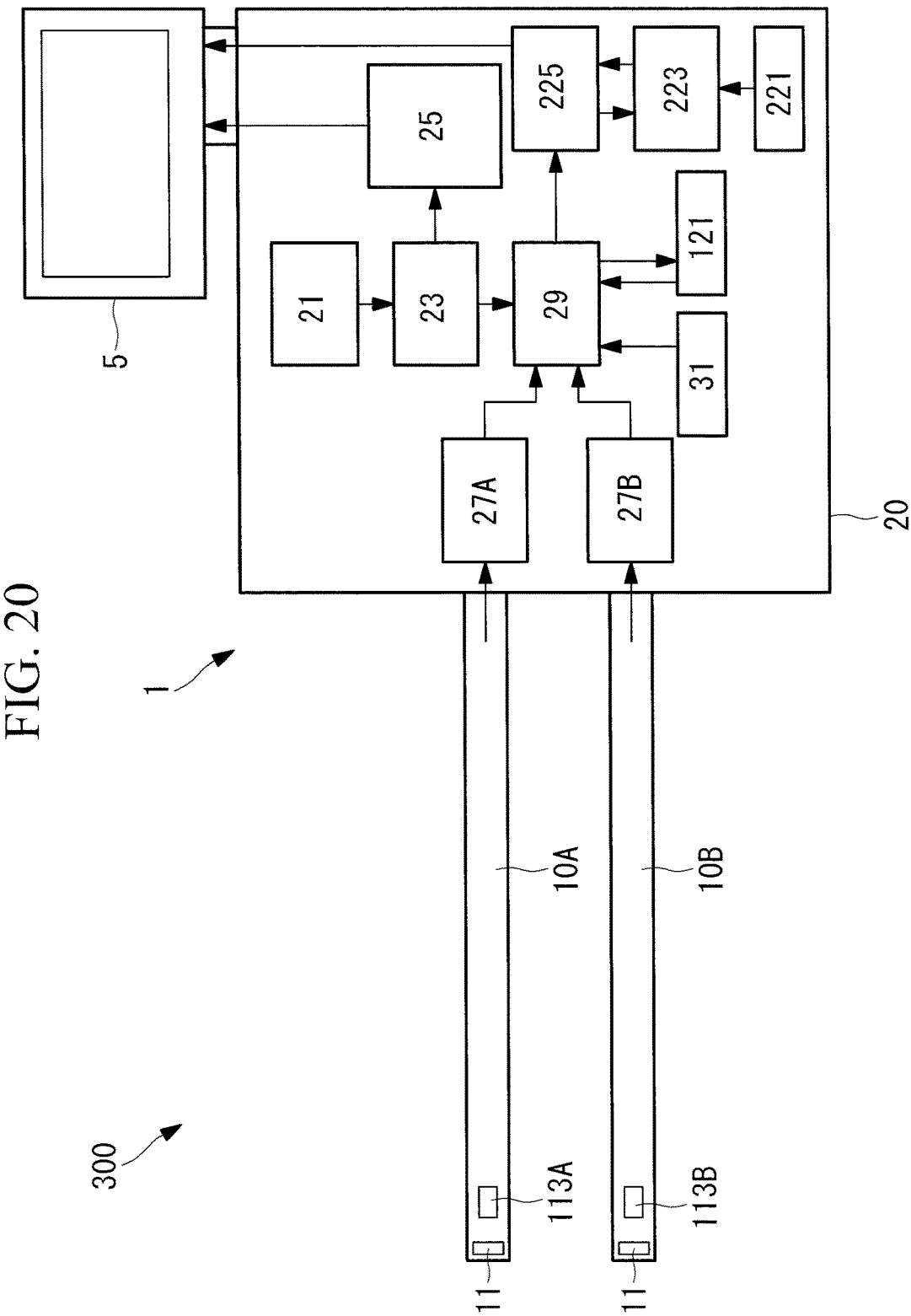
FIG. 20 is a configuration diagram illustrating, in outline, an endoscope device and a monitor of the medical system according to the third embodiment of the present invention.

As illustrated in FIG. 20, the main unit 20 of the endoscope device 1 further includes a memory 221 that stores the unique names of the various insertion portions 10A and 10B and the sheath units 3A and 3B; an OSD (on screen display) generating unit 223 that converts the character information of the unique names of the various insertion portions 10A and 10B stored in the memory 221 to video signals; and an image processing unit (control unit) 225 that carries out a process of superposing the video signals of the character information converted by the OSD generating unit 223 on an endoscopic image displayed on the monitor 5.

Figure 21:
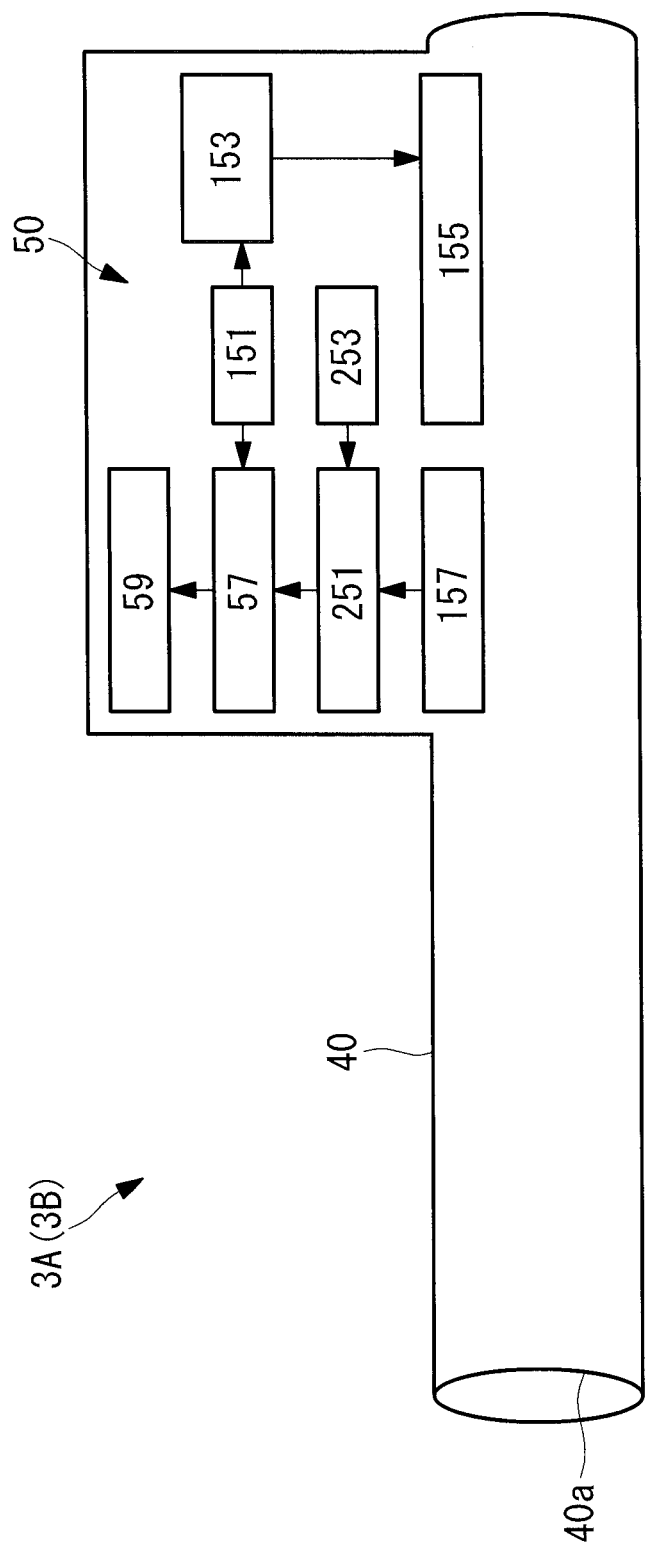
FIG. 21 is a configuration diagram illustrating, in outline, a sheath unit of the medical system according to the third embodiment of the present invention.

As illustrated in FIG. 21, the identification-signal generating units (identification-information output unit, outer-sleeve-information output unit) 50 of the sheath units 3A and 3B each further include a signal combining unit 251 that combines the electrical signals from the insertion portions 10A and 10B with the identification information (outer-sleeve identification information) unique to the sheath units 3A and 3B; and a memory 253 that stores the identification information of the sheath units 3A and 3B.

The operation of the medical system 300 having such a configuration will now be described.

Figure 22:
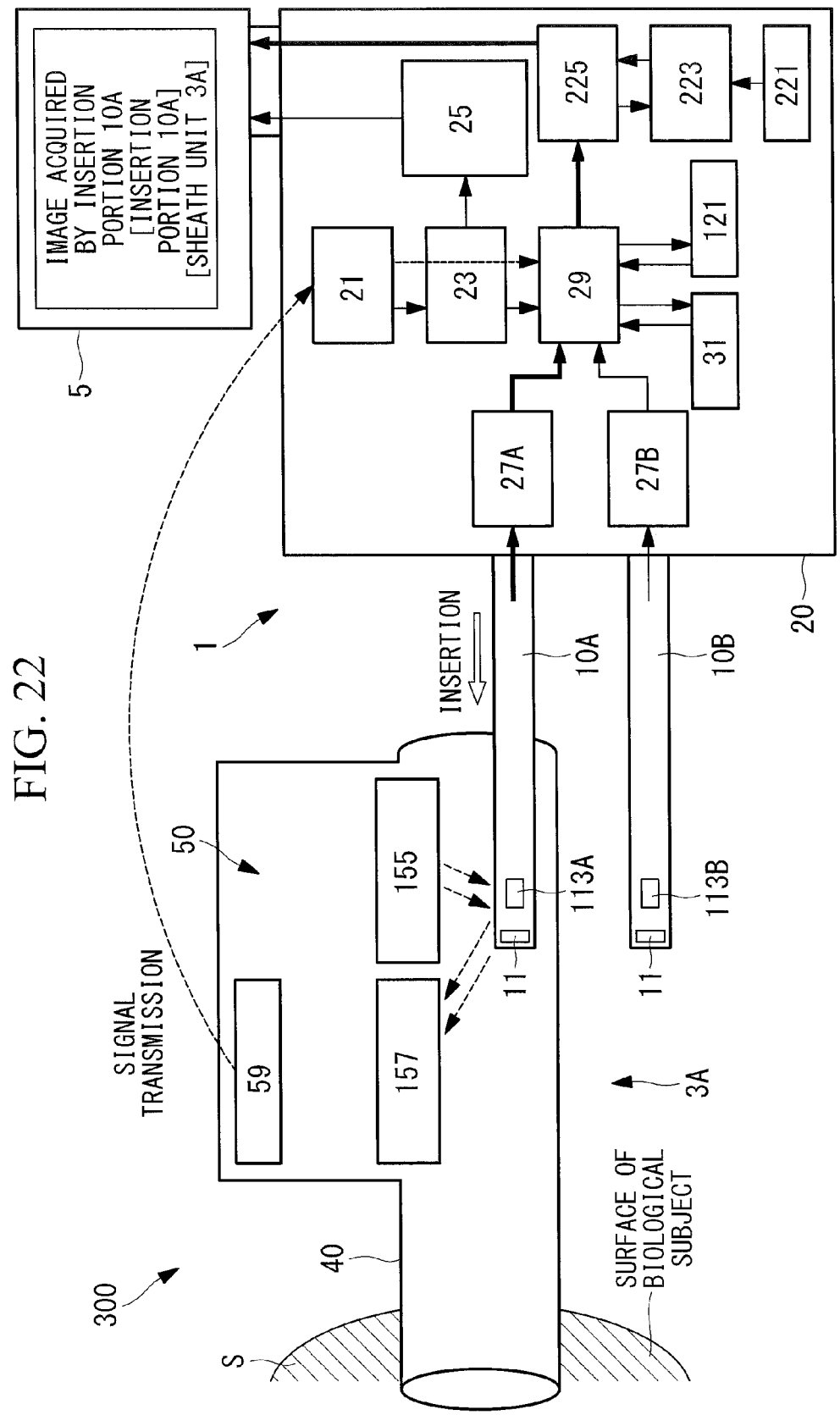
FIG. 22 is a diagram illustrating the insertion of one of the insertion portions into one of the sheath units, illustrated in FIG. 21, attached to the heart.

As illustrated in FIG. 22, in the medical system 300 according to this embodiment, when the insertion portion 10A is inserted into the sheath 40 of the sheath unit 3A and an electrical signal indicating the identification information from the RFID tag 113A is received by the reception antenna 157 of the identification-signal generating unit 50, the signal combining unit 251 combines the identification information of the electrical signal with the identification information of the sheath unit 3A stored in the memory 253 into a serial signal.

The combined serial signal is transmitted to the main unit 20 of the endoscope device 1 via the signal amplifying unit 57 and the transmission antenna 59 and is input to the image selector 29 and the power switching unit 25 via the reception antenna 21 and the signal converting unit 23. Then, the image selector 29 identifies the insertion portion 10A, which is currently in use (inserted in the body), and selects the video signal of the insertion portion 10A. In this way, the video signal of the selected insertion portion 10A, as well as each set of identification information of the insertion portion 10A and the sheath unit 3A, is transmitted to an image processing unit 225.

The image processing unit 225 transmits each set of identification information of the insertion portion 10A and the sheath unit 3A to the OSD generating unit 223. The OSD generating unit 223 reads out the character information ("insertion portion 10A" and "sheath unit 3A") of the insertion portion 10A and the sheath unit 3A corresponding to the identification information of the insertion portion 10A and the sheath unit 3A from the memory 221 and converts these to respective video signals. The video signals, i.e., the characters "insertion portion 10A" and "sheath unit 3A", acquired by the OSD generating unit 223 are superposed by the image processing unit 225 on the image acquired by the insertion portion 10A and are displayed on the monitor 5.

Figure 23:
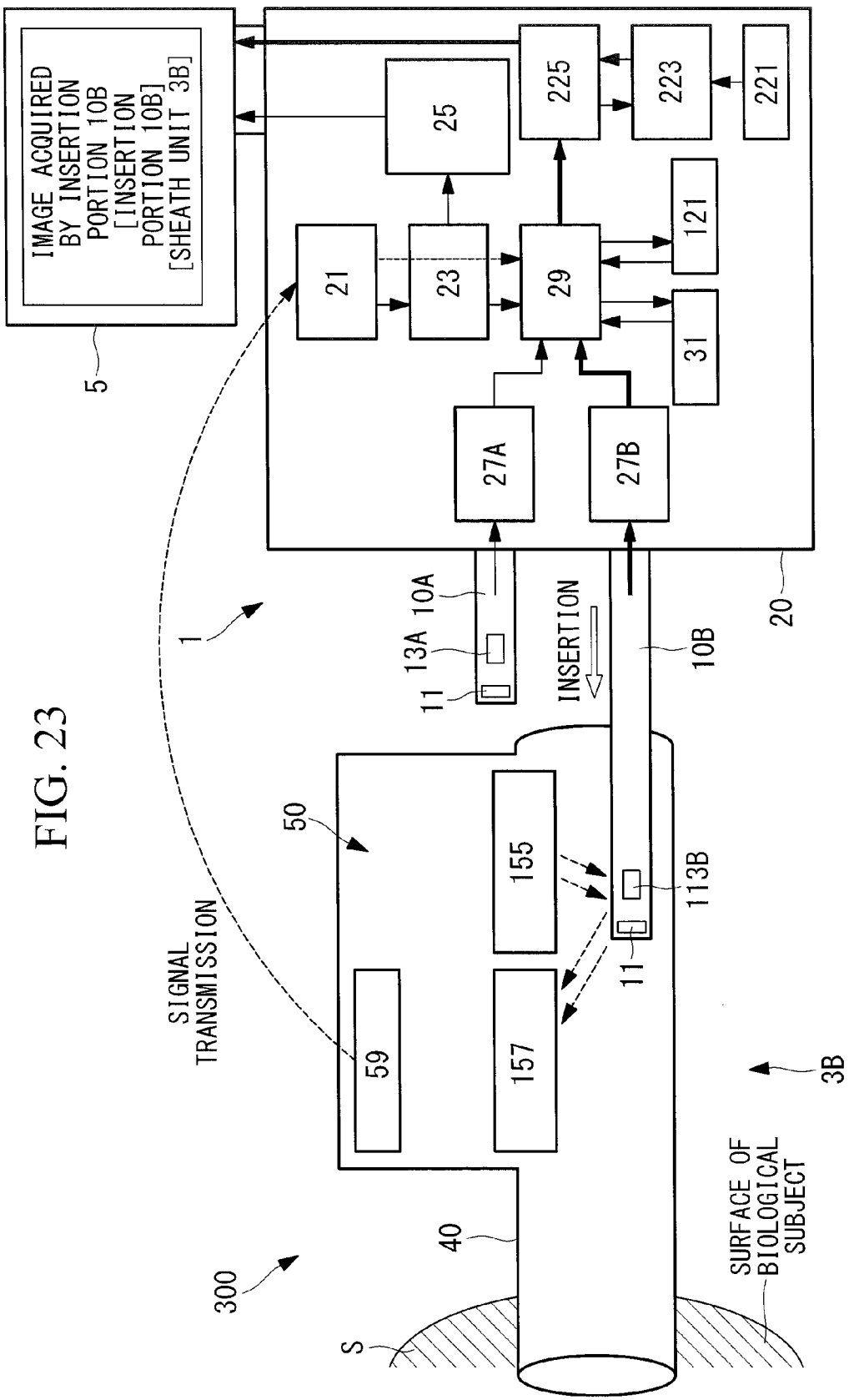
FIG. 23 is a diagram illustrating the insertion of the other insertion portion into one of the sheath units, illustrated in FIG. 21, attached to the heart.

As illustrated in FIG. 23, the basic operation of a case where the insertion portion 10B is inserted into the sheath unit 3B is the same as a case where the insertion portion 10A is inserted. Upon selection of the video signal of the insertion portion 10B by the image selector 29, the selected image, as well as the identification information of the insertion portion 10B and the sheath unit 3B, is transmitted to the image processing unit 27.

The image processing unit 27 transmits each set of identification information of the insertion portion 10B and the sheath unit 3B to the OSD generating unit 223, and the OSD generating unit 223 reads out the character information of the insertion portion 10B and the sheath unit 3B ("insertion portion 10B" and "sheath unit 3B") corresponding to the identification information from the memory 221 and converts these to video signals.

Then, the video signals, i.e., the characters "insertion portion 10B" and "sheath unit 3B", acquired by the OSD generating unit 223 are superposed by the image processing unit 225 on the image acquired by the insertion portion 10B and are displayed on the monitor 5. This is also the same for cases where the insertion portion 10A is inserted into the sheath unit 3B and where the insertion portion 10B is inserted into the sheath unit 3A.

Figure 24:
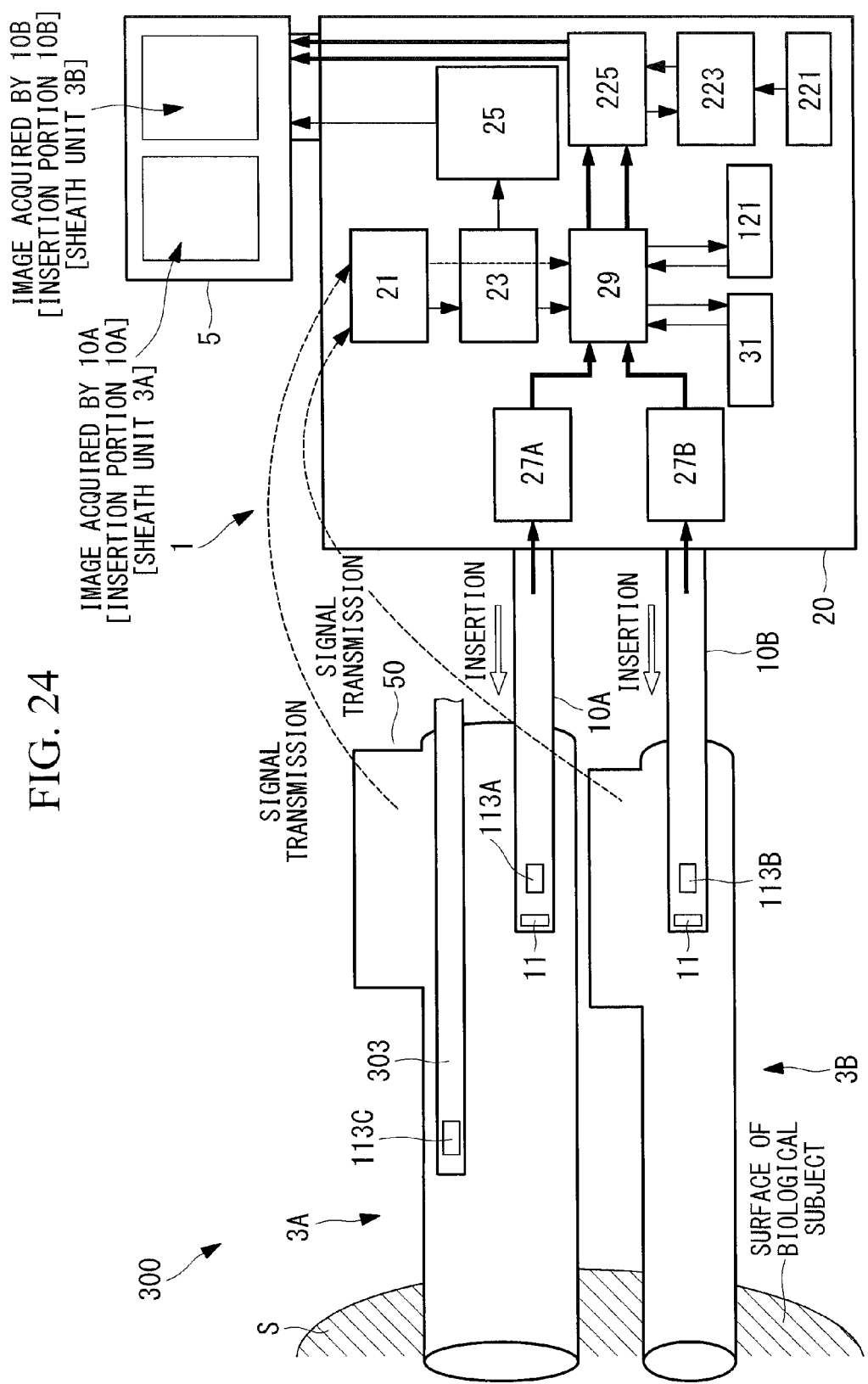
FIG. 24 is a diagram illustrating the insertion of the insertion portions into two sheath units attached to the heart.

As illustrated in FIG. 24, in this embodiment, for example, the sheath unit 3A and the sheath unit 3B may both be attached to the biological subject S; the insertion portion 10A and a medical-treatment device (insertion portion) 303 for medically treating an affected site may be inserted into the sheath unit 3A; and the insertion portion 10B may be inserted into the sheath unit 3B. The code of the RFID tag of the medical-treatment device 303 is "113C".

In such a case, the display setting of the monitor 5 may be picture-in-picture or 2win. In this way, the monitor 5 simultaneously displays both the image acquired by the insertion portion 10A and the image acquired by the insertion portion 10B. Furthermore, the characters "endoscope insertion portion 10A", "medical-treatment device 303", and "sheath unit 3A" are superposed and displayed on the image acquired by the insertion portion 10A, and the characters "endoscope insertion portion 10B" and "sheath unit 3B" are superposed and displayed on the image acquired by the insertion portion 10B.

As described above, the medical system 300 according to this embodiment enables immediate understanding of the relationship among the sheath units 3A and 3B, the insertion portions 10A and 10B, and so forth on the monitor 5. In a case where a plurality of insertion portions 10A and 10B of the endoscope device 1 are inserted using a plurality of sheath units 3A and 3B, there has been a problem in that, for example, if the tips of the insertion portion 10A and the insertion portion 10B face each other in the body, it cannot be determined from the image which one of the insertion portions 10A and 10B is inserted into the sheath unit 3A or 3B and which one of the images acquired by the insertion portions 10A and 10B is displayed on the monitor 5. According to this embodiment, the correspondence among the images, the insertion portions 10A and 10B, and the sheath units 3A and 3B and the mutual relationship between the insertion portions 10A and 10B and the sheath units 3A and 3B can always be immediately understood. Thus, it is possible to reduce the burden on the operator, to improve safety, and to reduce the surgery time.

Furthermore, the use of the RFID tags 113A and 113B as identification-information generating portions enables immediate identification of all devices inserted (simultaneous identification of multiple devices) even when a plurality of devices, such as the insertion portions 10A and 10B and the treatment device 303, are simultaneously inserted into a single sheath unit 3, and thus, time saving is possible.

In this embodiment, the OSD display on the monitor 5 is described as an example of the way of notifying the operator about the insertion portions 10A and 10B; instead of this, for example, a small liquid-crystal character display monitor may be disposed on the base of the sheath unit 3 to display, on the monitor 5, the names of the insertion portions 10A and 10B inserted into the sheath 40.

Fourth Embodiment

A medical system according to a fourth embodiment of the present invention will now be described.

Figure 25:
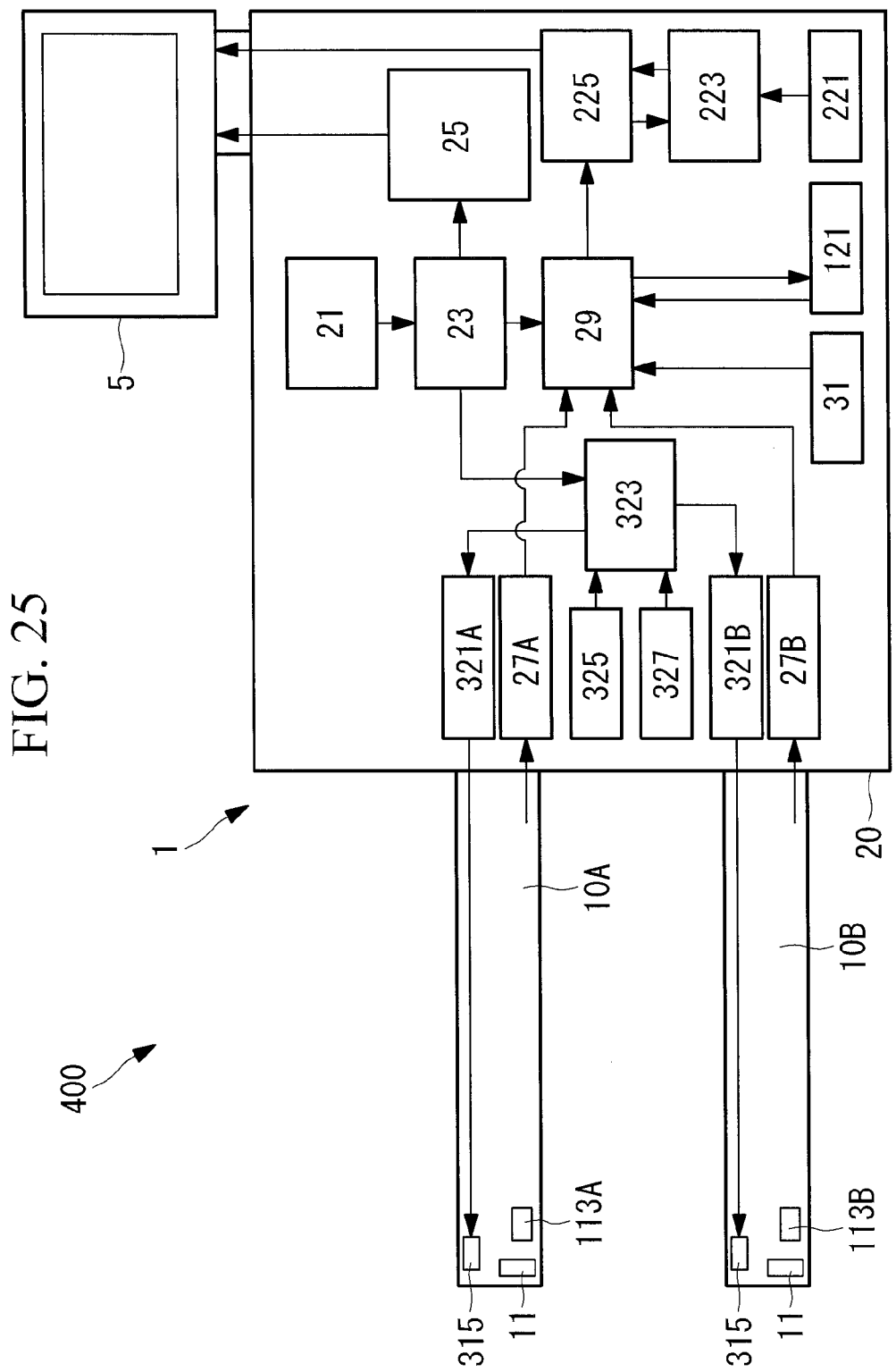
FIG. 25 is a configuration diagram illustrating, in outline, an endoscope device and a monitor of a medical system according to a fourth embodiment of the present invention.

As illustrated in FIG. 25, a medical system 400 according to this embodiment differs from the first to third embodiments in that the insertion portions 10A and 10B each have a illumination LED (illumination light source) 315 that emit illumination light capable of illuminating the inside of a body cavity in a biological subject.

Hereinafter, components that have the same configuration as those in the medical systems 100, 200, and 300 according to the first to third embodiments are designated by the same reference numerals, and descriptions thereof are omitted.

The illumination LED 315 is disposed at the tip of each of the insertion portions 10A and 10B.

The main unit 20 further includes LED driving units (control units) 321A and 321B that supply electric power to the illumination LEDs 315; an LED control unit (control unit) 323 that generates control signals for adjusting the emission brightness of the illumination LEDs 315; a memory (storage unit) 325 that stores the data arrays associated with the identification information (insertion-portion identification information) of each of the insertion portions 10A and 10B; and a memory (storage unit) 327 that temporarily stores electrical signals transmitted from the signal converting unit 23 during insertion/removal of the insertion portions 10A and 10B.

The operation of the medical system 400 having such a configuration will now be described with reference to the flow chart in FIG. 26.

Figure 26:
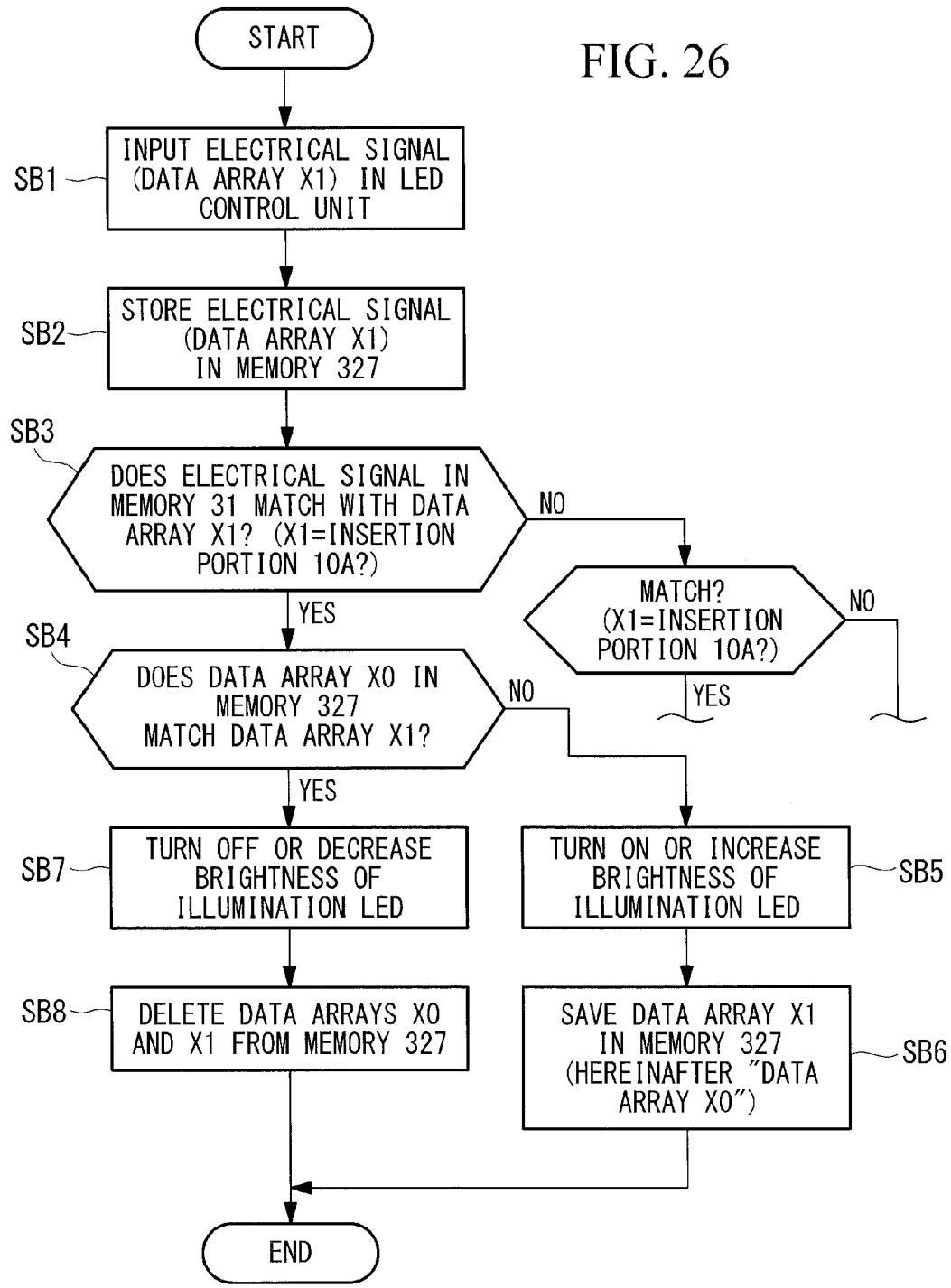
FIG. 26 is a flow chart showing the examination of the heart by the medical system according to the fourth embodiment of the present invention.

Referring to FIG. 26, similarly to FIG. 16, X0 represents the preceding data array of the identification information stored in the memory 327, and X1 represents the subsequent data array.

Figure 27:
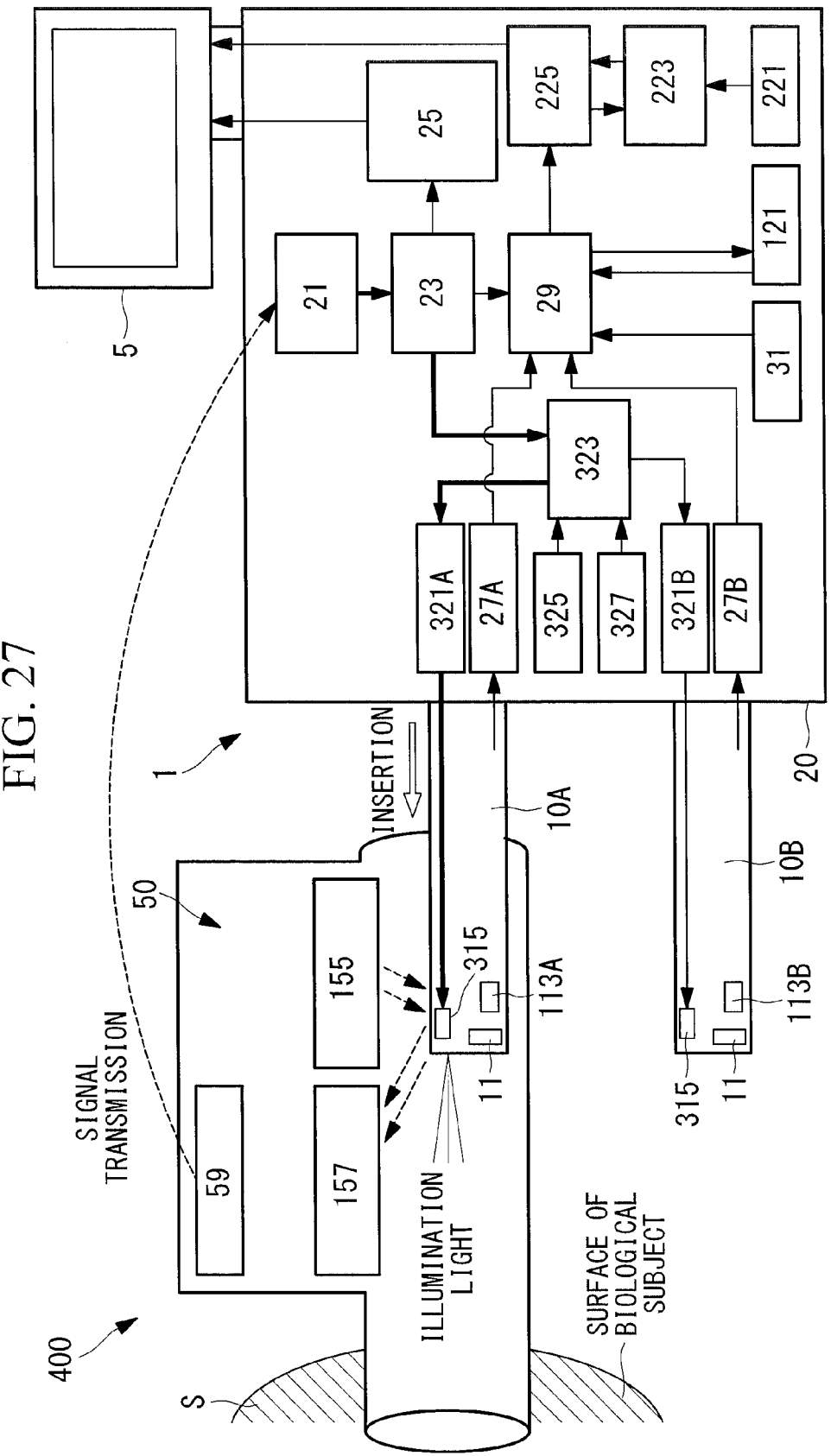
FIG. 27 is a diagram illustrating the insertion of the other insertion portion into one of the sheath units attached to the heart.

As illustrated in FIG. 27, in the medical system 400 according to this embodiment, upon insertion of the insertion portion 10A into the sheath 40 of the sheath unit 3A, an electrical signal from the RFID tag 113A is received by the reception antenna 157, and an electrical signal indicating the identification information of the insertion portion 10A is acquired by the identification-signal generating unit 50.

The electrical signal acquired by the identification-signal generating unit 50 is transmitted from the transmission antenna 59 to the main unit 20, is received by the reception antenna 21, and is input to the image selector 29, the power switching unit 25, and the LED control unit 323 via the signal converting unit 23 (Step SB1).

The LED control unit 323 inputs the electrical signal sent from the signal converting unit 23 to the memory 327 for temporary storage (Step SB2), checks for a match between the data array of the electrical signal and the data array of identification information stored in the memory 325 (Step SB3), and recognizes the insertion portion 10A as currently being inserted into the sheath unit 3 since, as a result of match checking, a match is found with the data array of the identification data in the memory 325.

Then, the electrical signal indicating the identification information of the insertion portion 10A temporarily stored in the memory 327 is sent to the LED control unit 323. The LED control unit 323 compares the subsequent data array X1 of the electrical signal transmitted from the signal converting unit 23 with the preceding data array X0 of the electrical signal input from the memory 327 (Step SB4). With regard to the insertion operation of the insertion portion 10A, the two signals have different data arrays.

If it is determined by the LED control unit 323 that the data arrays differ, the LED control unit 323 recognizes that the insertion operation has been performed, and an instruction for illumination of the illumination LED 315 or an instruction for increasing the emission brightness of the illumination LED 315 in a case where the illumination LED 315 is already illuminated is input to the LED driving unit 321A.

The LED driving unit 321A illuminates the illumination LED 315A or increases the emission brightness of the illumination LED 315 in response to the instruction from the LED control unit 323 (Step SB5). In such a case, the data arrays of the identification information stored in the memory 327 are saved (Step SB6).

The identification of the insertion portions 10A and 10B by the image selector 29 is the same as that in the third embodiment, and thus, a description thereof is omitted.

Figure 28:
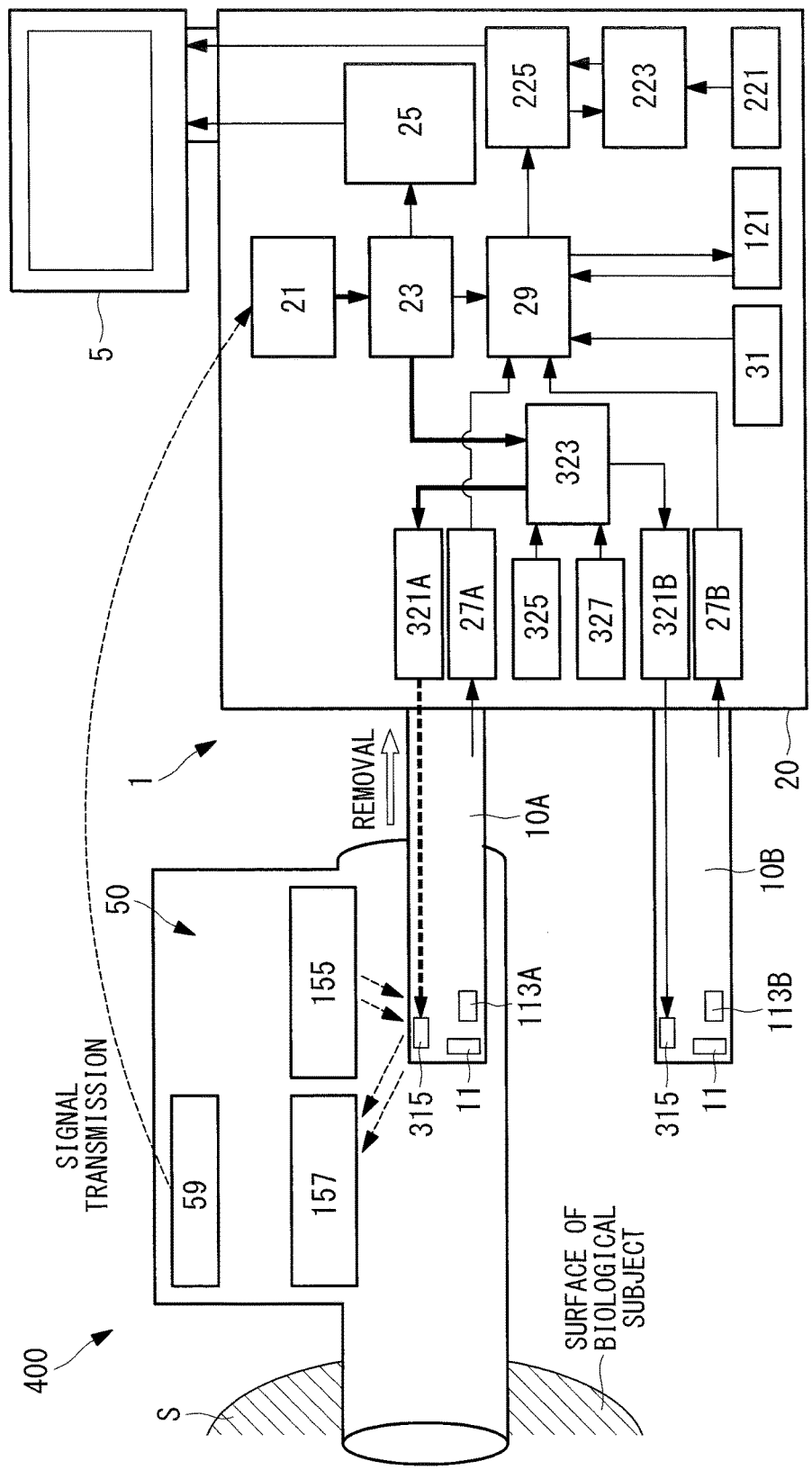
FIG. 28 is a diagram illustrating the removal of the other insertion portion from the sheath unit illustrated in FIG. 27.

As illustrated in FIG. 28, subsequently, upon removal of the insertion portion 10A from the sheath unit 3, similar to insertion, an electrical signal from the RFID tag 113A is received by the reception antenna 157, and an electrical signal indicating the identification information of the insertion portion 10A is acquired by the identification-signal generating unit 50.

The electrical signal acquired by the identification-signal generating unit 50 is transmitted from the transmission antenna 59 to the main unit 20, is received by the reception antenna 21, and is input to the image selector 29, the power switching unit 25, and the LED control unit 323 via the signal converting unit 23 (Step SB1).

The LED control unit 323 inputs the electrical signal sent from the signal converting unit 23 to the memory 327 for temporary storage (Step SB2), checks for a match between the data array of the electrical signal and the data array of identification information stored in the memory 325 (Step SB3), and recognizes the insertion portion 10A as currently being inserted into the sheath unit 3 since, as a result of match checking, a match is found with the identification data in the memory 325.

Then, the electrical signal temporarily stored in the memory 327 is sent to the LED control unit 323. The array data of the electrical signal is the data transmitted from the signal converting unit 23 during insertion of the insertion portion 10A into the sheath unit 3.

The LED control unit 323 compares the data array X1 of the electrical signal transmitted from the signal converting unit 23 with the data array X0 of the electrical signal temporarily stored in the memory 327 (Step SB4). If it is determined that the data arrays X1 and X0 match, the LED control unit 323 recognizes that the removal operation has been performed, and an instruction for lowering the emission brightness of the illumination LED 315 or an instruction for turning off the illumination LED 315 is input to the LED driving unit 321A.

Figure 29:
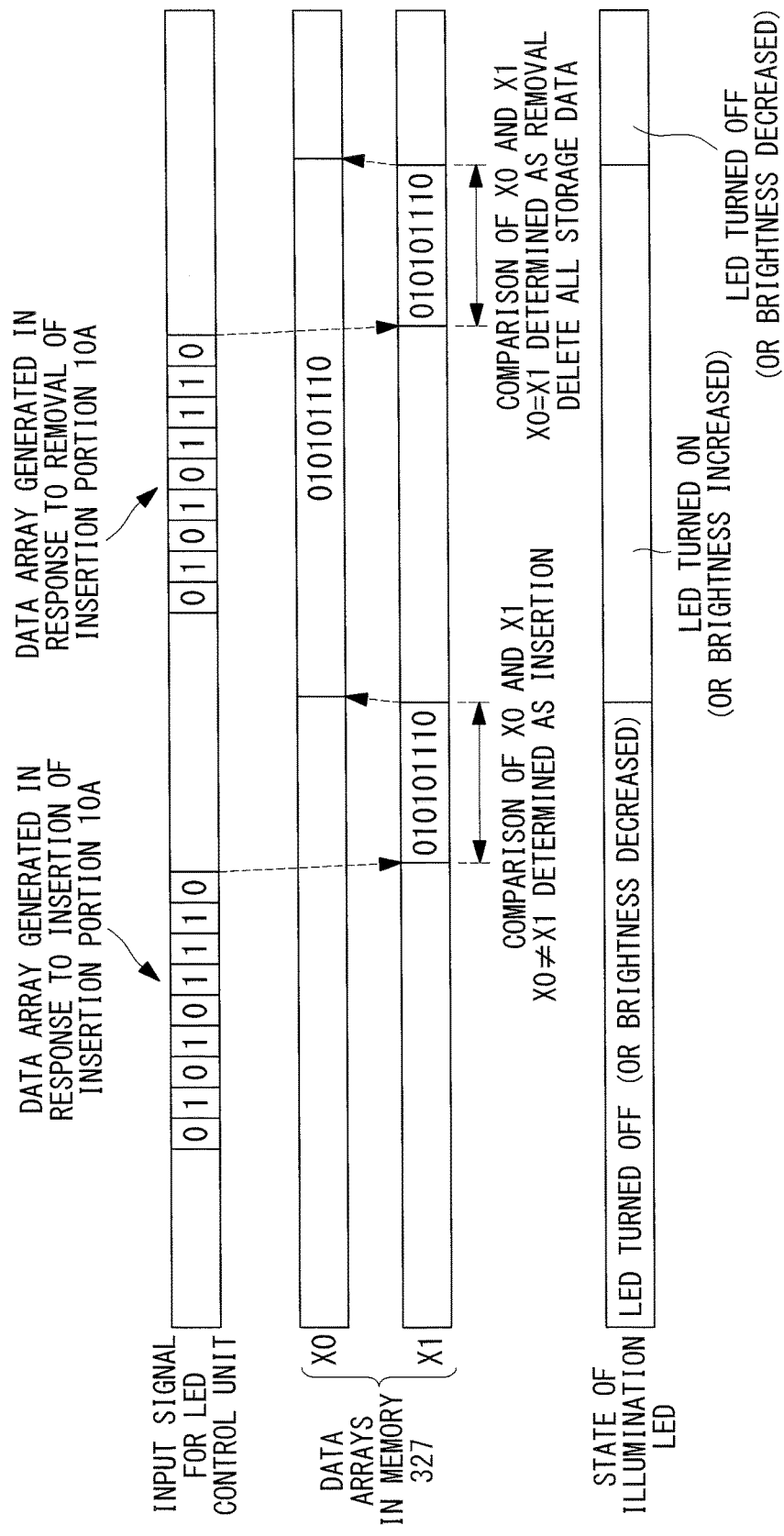
FIG. 29 is a diagram illustrating the relationship among the data array of an electrical signal of the identification information input to an LED control unit, a preceding data array and a subsequent data array of identification information stored in a memory, and the illumination state of an illumination LED.

The LED driving unit 321A reduces the emission brightness of the illumination LED 315 or turns off the illumination LED 315 in response to the instruction from the LED control unit 323 (Step SB7). In such a case, the LED control unit 323 deletes all of the identification-signal data stored in the memory 325 (Step SB8). FIG. 29 illustrates the relationship among the data array of the electrical signal of the identification information input to the LED control unit 323, the preceding data array X0 and subsequent data array X1 of the identification information stored in the memory 327, and the illumination state of the illumination LED 315.

A case where the insertion portion 10B is inserted into the biological subject S and a case where it is removed from the biological subject S are the same as those of the insertion portion 10A, and thus, a description thereof is omitted.

As described above, the medical system 400 according to this embodiment automatically varies the illumination light for illuminating the inside of the body cavity in the biological subject with the illumination LED 315 in cooperation with the insertion operation and the removal operation of the insertion portions 10A and 10B to and from the inside of the body cavity in the biological subject. In this way, the operation burden on the operator can be reduced, and blocking of the view can be prevented.

For example, if the insertion portion 10A or 10B is illuminated even when disposed outside the body, the light may enter the view of the operator, interfering with the surgery. The light may be turned off manually when not in use, but if the insertion portions are frequently switched during surgery, the illumination light must be frequently turned on and off, resulting in complicated operations. In this embodiment, if the insertion portion 10A or 10B is outside the body, the illumination LED 315 is dimmed or turned off, whereas if the insertion portion 10A or 10B is inserted in the body, the illumination LED 315 is turned on or brightened to enable efficient examination.

In this embodiment, the illumination LEDs 315 are disposed at the tips of the insertion portions 10A and 10B; instead of this, for example, fibers may be disposed along the longitudinal directions of the insertion portions 10A and 10B, and illumination LEDs may be disposed at the bases of the fibers to guide the light from the illumination LEDs to the tips of the insertion portions 10A and 10B via the fibers.

In this embodiment, although the insertion portions 10A and 10B are identified by the REID tags 113A and 113B, instead of this, as in the first embodiment, the configuration may be such that the insertion portions 10A and 10B are identified by the barcodes 13A and 13B, and the illumination LEDs 315 may be turned on/off or the illumination brightness may be increased/decreased in cooperation with the insertion operation and removal operation of the insertion portions 10A and 10B, which are determined by reading the barcodes 13A and 13B.

Fifth Embodiment

A medical system according to a fifth embodiment of the present invention will now be described.

Figure 30:
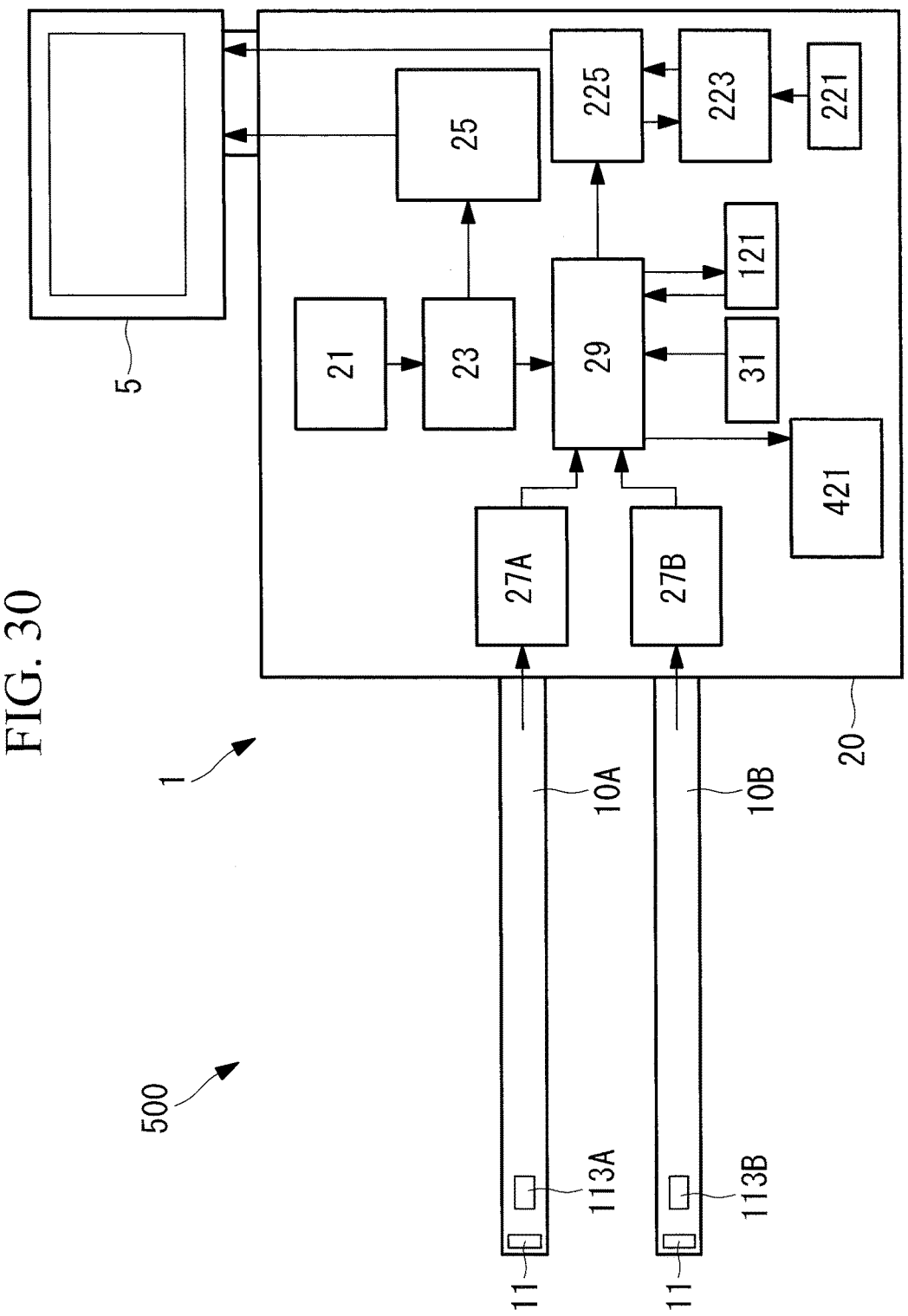
FIG. 30 is a configuration diagram illustrating, in outline, an endoscope device and a monitor of a medical system according to a fifth embodiment of the present invention.

As illustrated in FIG. 30, a medical system 500 according to this embodiment differs from the first to fourth embodiments in that the main unit 20 of the endoscope device 1 includes a moving-image recording unit (image recording unit) 421 that records a moving image sent from the image processing units 27A or 27B to the image processing unit 225.

Hereinafter, components that have the same configuration as those in the medical systems 100, 200, 300, and 400 according to the first to fourth embodiments are designated by the same reference numerals, and descriptions thereof are omitted.

The image selector 29 compares the data array of the identification information of the newly identified insertion portion 10A or the insertion portion 10B with the data array of the identification information stored immediately before in the memory (storage unit) 121, records the image acquired by the newly identified insertion portion 10A or the insertion portion 10B in the moving-image recording unit 421 when these data arrays differ, and stops the recording performed by the moving-image recording unit 421 when these data arrays match.

The operation of the medical system 500 having such a configuration will be described with reference to the flow chart in FIG. 31.

Figure 31:
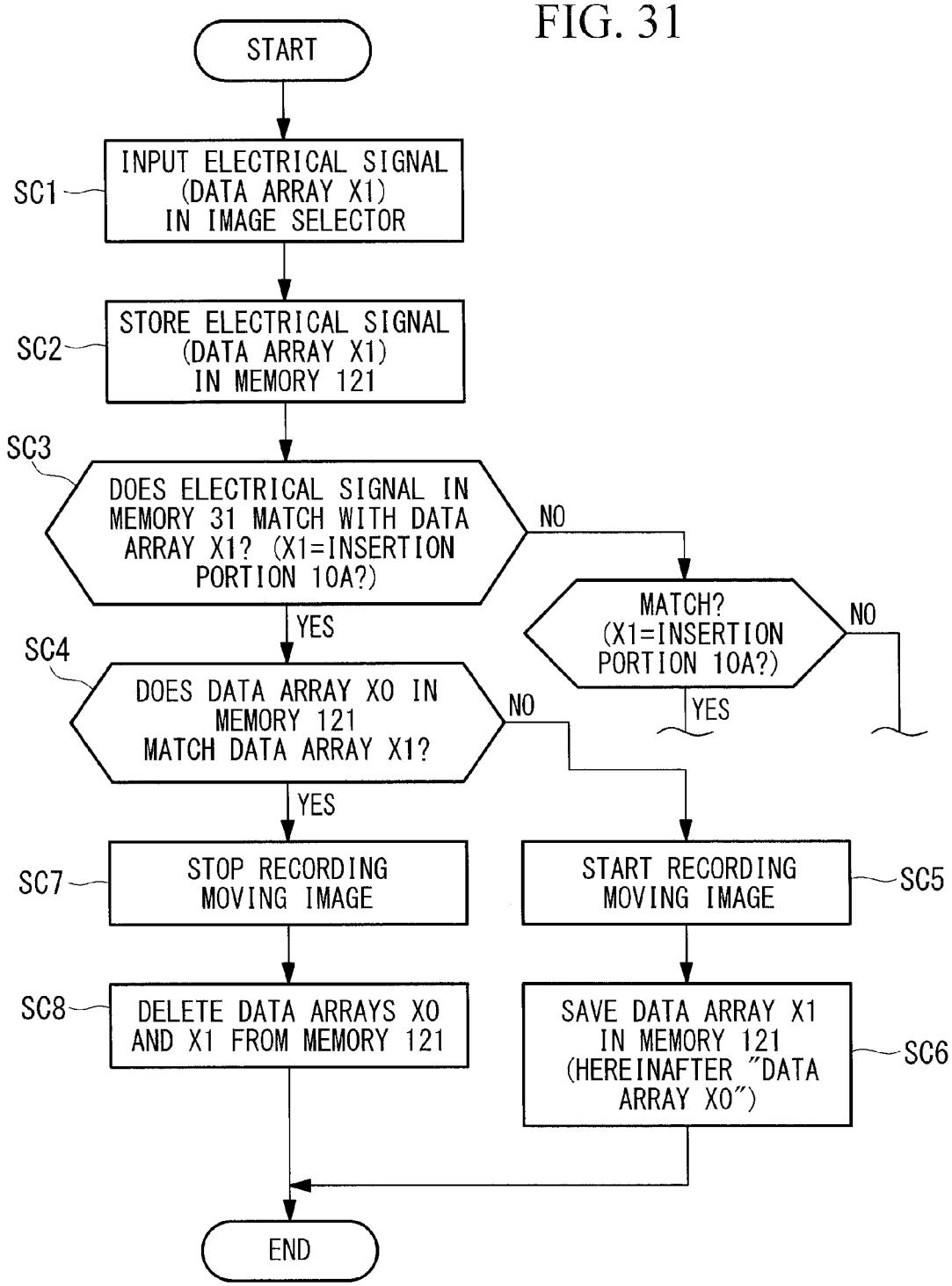
FIG. 31 is a flow chart for explaining examination of the heart with the medical system according to the fifth embodiment of the present invention.

Referring to FIG. 31, similarly to FIG. 16, X0 represents the preceding data array of the identification information stored in the memory 121, and X1 represent the subsequent data array.

Figure 32:
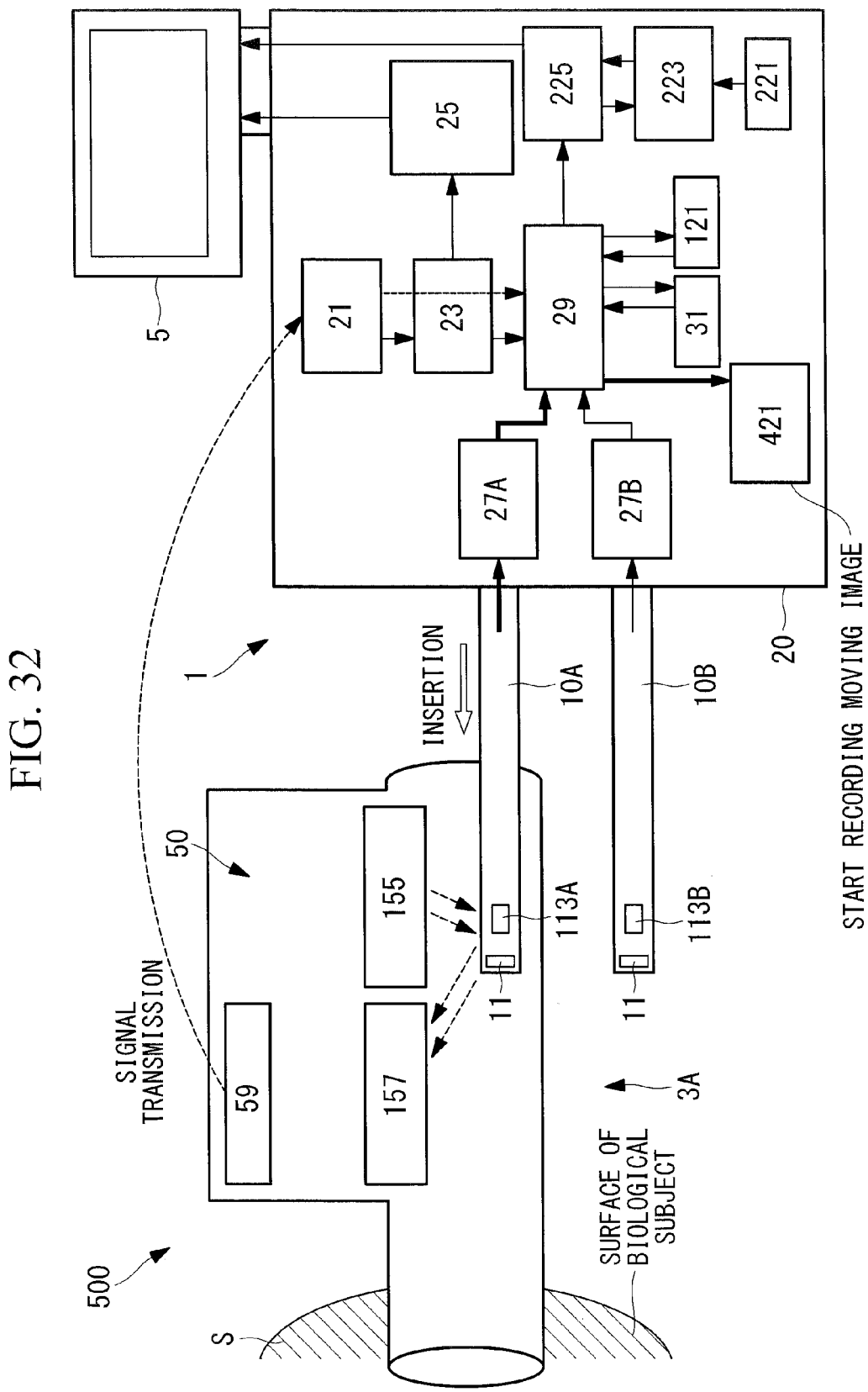
FIG. 32 is a diagram illustrating the insertion of one of the insertion portions into one of the sheath units attached to the heart.

As illustrated in FIG. 32, in the medical system 500 according to this embodiment, upon insertion of the insertion portion 10A into the sheath unit 3 and input of an electrical signal indicating the identification information of the insertion portion 10A acquired by the identification-signal generating unit 50 (Step SC1), the electrical signal transmitted from the signal converting unit 23 is temporarily stored in the memory 121 (Step SC2) while the image selector 29 checks for a match between the data array of the latest electrical signal and the data array of the identification information stored in the memory 31 (Step SC3).

Since a match is found, the image selector 29 recognizes that the insertion portion 10A as currently being inserted into the sheath unit 3. Subsequently, the electrical signal indicating the identification information sent during the previous insertion/removal operation is temporarily stored in the memory 121 and is then sent to the image selector 29. The electrical signal of the identification information stored in the memory 121 is overwritten every time an electrical signal is input.

The image selector 29 compares the data array X1 of the latest electrical signal transmitted from the signal converting unit 23 with the data array X0 of the electrical signal temporarily stored in the memory 121 (Step SC4). With regard to the insertion operation of the insertion portion 10A, the two electrical signals have different data arrays.

If the image selector 29 determines that the data arrays X0 and X1 differ, an instruction is sent to the moving-image recording unit 421 to start recording the moving image. The moving-image recording unit 421 records the video signal transmitted from an image processing unit 27A in accordance with the instruction from the image selector 29 (Step SC5). In this case, the data array of the identification information stored in the memory 121 is saved (Step SC6).

Figure 33:
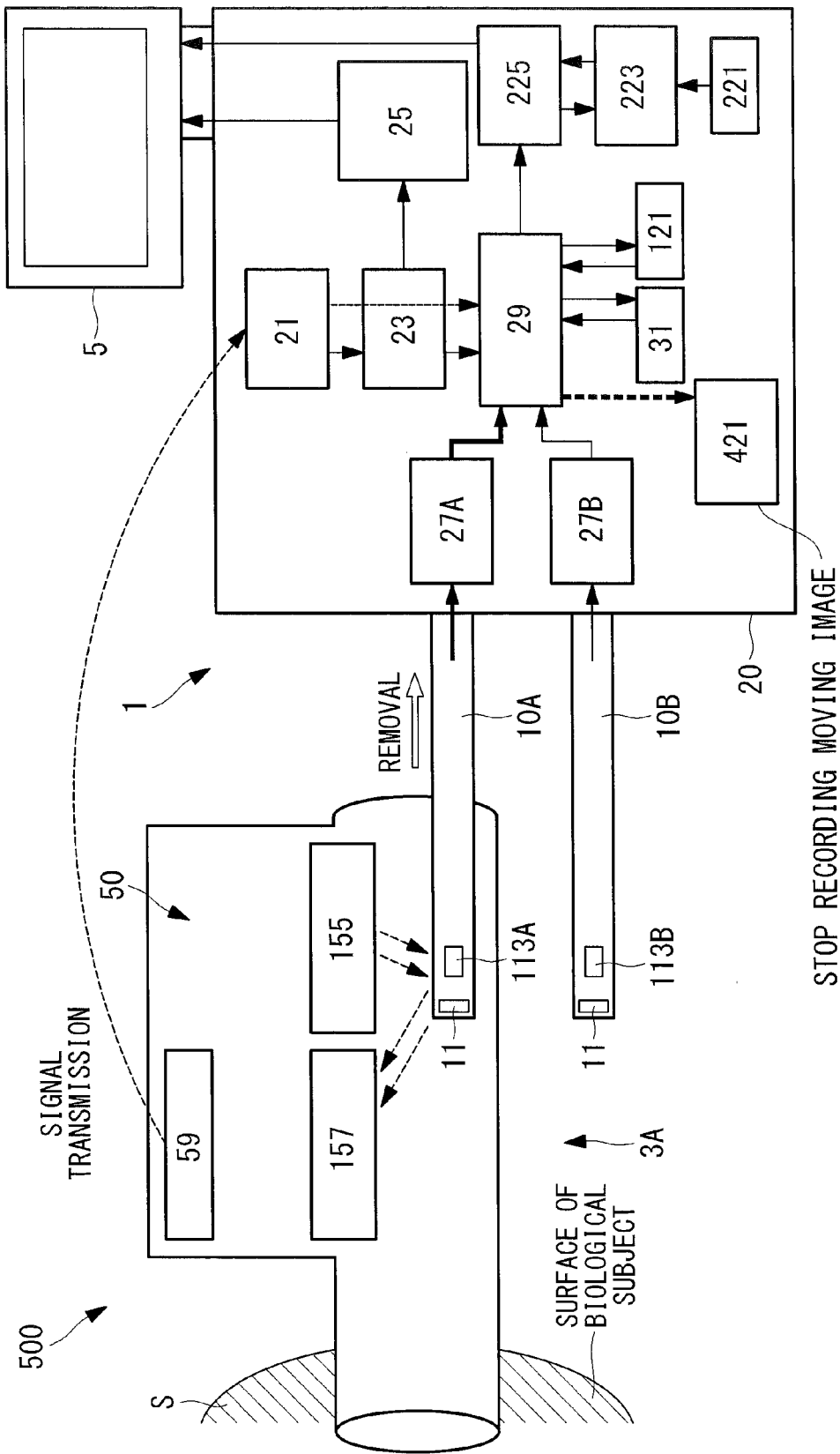
FIG. 33 is a diagram illustrating the removal of one of the insertion portions from the sheath unit illustrated in FIG. 27.

Subsequently, as illustrated in FIG. 33, upon removal of the insertion portion 10A from the sheath unit 3, similarly to insertion, the electrical signal acquired by the identification-signal generating unit 50 is input to the image selector 29 and the power switching unit 25 (Step SC1). Then, the electrical signal transmitted from the signal converting unit 23 is temporarily stored in the memory 121 (Step SC2) while the image selector 29 checks for a match between the data array of the latest electrical signal and the data array of the identification information stored in the memory 31 (Step SC3) and recognizes the insertion portion 10A as currently being inserted into the sheath unit 3 since, as a result of the match checking, a match is found with the data arrray of the identification information in the memory 31.

Then, the electrical signal temporarily stored in the memory 121 is sent to the image selector 29. The data array of the electrical signal is data that is transmitted by the signal converting unit 23 at the time of insertion of the insertion portion 110A into the sheath unit 3.

The image selector 29 compares the data array X1 of the electrical signal transmitted from the signal converting unit 23 with the data array X0 of the electrical signal temporarily stored in the memory 121 (Step SC4). With regard to the insertion/removal operation of the insertion portion 10A, the two signals have the same data arrays. If the image selector 29 determines that these data arrays X0 and X1 match, it is recognized that the removal operation has been carried out, and an instruction for stopping the recording of the moving image is sent to the moving-image recording unit 421.

Figure 34:
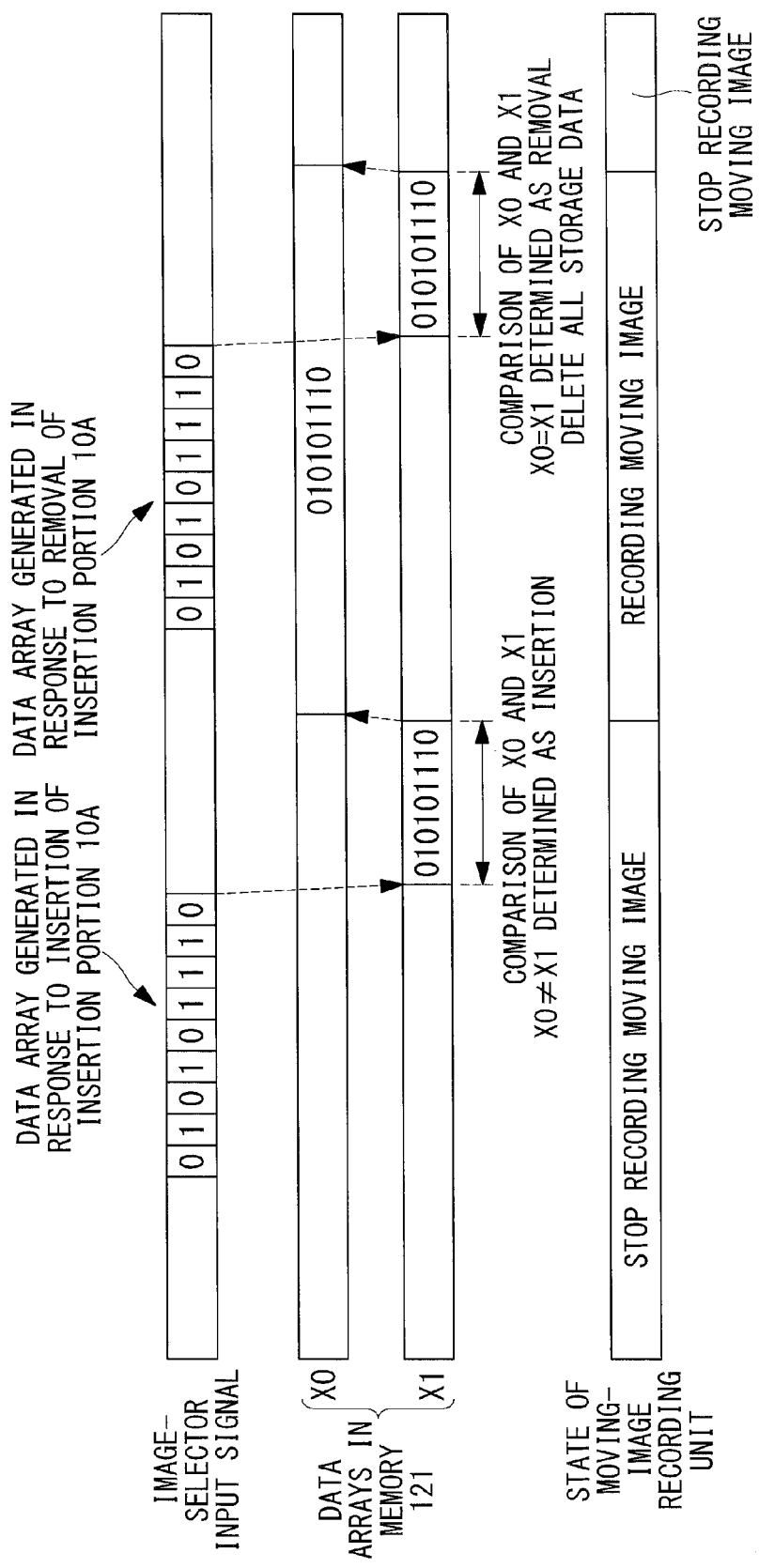
FIG. 34 illustrates the relationship among the data array of an electrical signal of the identification information input to an image selector, a preceding data array and a subsequent data array of identification information stored in a memory, and the recording state of a moving-image recording unit.

The moving-image recording unit 421 stops the recording of the moving image in accordance with the instruction from the image selector 29 (Step SC7). In this case, the image selector 29 deletes the data array of the identification information stored in the memory 121 (Step SC8) to reset it. FIG. 34 illustrates the relationship among the data array of the electrical signal of the identification information input to the image selector 29, the preceding data array X0 and subsequent data array X1 of the identification information stored in the memory 121, and the recording state of the moving-image recording unit 421.

The case of the insertion portion 10B is the same as the case of insertion portion 10A, and thus a description thereof is omitted.

In the medical system 500 according to this embodiment, the image acquired by the insertion portion 10A is stored in the image recording unit 421 so long as the same insertion portion 10A of the endoscope device 1 is inserted into the body cavity in the biological subject, and image recording by the image recording unit 421 is stopped upon removal of the insertion portion 10A from the body cavity in the biological subject; in this way, it is possible to efficiently record only desired images of the inside of the body cavity in the biological subject every time the insertion portion 10A or 10B to be used is switched.

In this embodiment, although the insertion portions 10A and 10B are identified by the RFID tags 113A and 113B, as described in the first embodiment, the configuration may be such that the insertion portions 10A and 10B are identified by the barcodes 13A and 13B, and the recording of the moving image may be started or stopped in cooperation with the insertion operation or removal operation of the insertion portion 10A or 10B identified by reading the barcode 13A or 13B. This is the same for the operation of increasing or decreasing the backlight brightness of the monitor 5.

The embodiments of the present invention have been described in detail above with reference to the drawings; the specific configuration, however, is not limited to the embodiments, and design modifications within a range that does not depart from the scope of the invention are also included in the present invention. For example, the present invention is not limited to that applied to the embodiments described above and instead may be applied to embodiments in which the above-described embodiments are appropriately combined; the present invention is not particularly limited. Furthermore, for example, in the embodiments described above, although the endoscope device 1 including endoscope-like insertion portions 10A and 10B is described as an example medical device, instead, a treatment device including a treatment tool-like insertion portion for medically treating an affected site may be employed as the medical device. Furthermore, although the barcodes 13A and 13B and the RFID tags 113A and 113B are described as examples of unique identification information sources, instead, magnetic chips or an optical communication means may be employed.

Furthermore, for example, in the embodiments described above, although the sheath 40 is described as an example of an outer sleeve, instead, for example, a trocar or an introducer may be used so long as it guides the insertion portion 10A or 10B through a through-hole into a body cavity when the insertion portion 10A or 10B is to be inserted into the body cavity in a biological subject. Furthermore, in the embodiments described above, although the identification-signal generating unit 50 is described as being embedded in the sheath 40, instead, the identification-signal generating unit 50 may be disposed detachable from the sheath 40 or may be disposed near the sheath 40.

Furthermore, in these embodiments, for example, the image selector 29 may compare the data array X1 of the identification information of the newly identified insertion portion 10A or 10B with the data array X0 of the identification information stored in the memory 121 immediately before, and may increase the backlight brightness of the monitor 5 if these data arrays X0 and X1 differ and reduce the backlight brightness of the monitor 5 if these data arrays X0 and X1 match.

In this way, the monitor 5 is bright while the insertion portion 10A or 10B is being operated inside the body cavity in the biological subject, and the monitor 5 is darkened upon removal of the insertion portion from the body cavity in the biological subject. Thus, wasteful power consumption can be suppressed.

Furthermore, in the embodiments described above, although the barcodes 13A and 13B or the RFID tags 113A and 113B are provided on the insertion portions 10A and 10B, and the sheath unit 3 includes the identification-signal generating unit 50, instead, the insertion portions 10A and 10B may include the identification-signal generating units 50, and the barcodes 13A and 13B or the RFID tags 113A and 113B may be provided on the sheath units 3.

Figure 35:
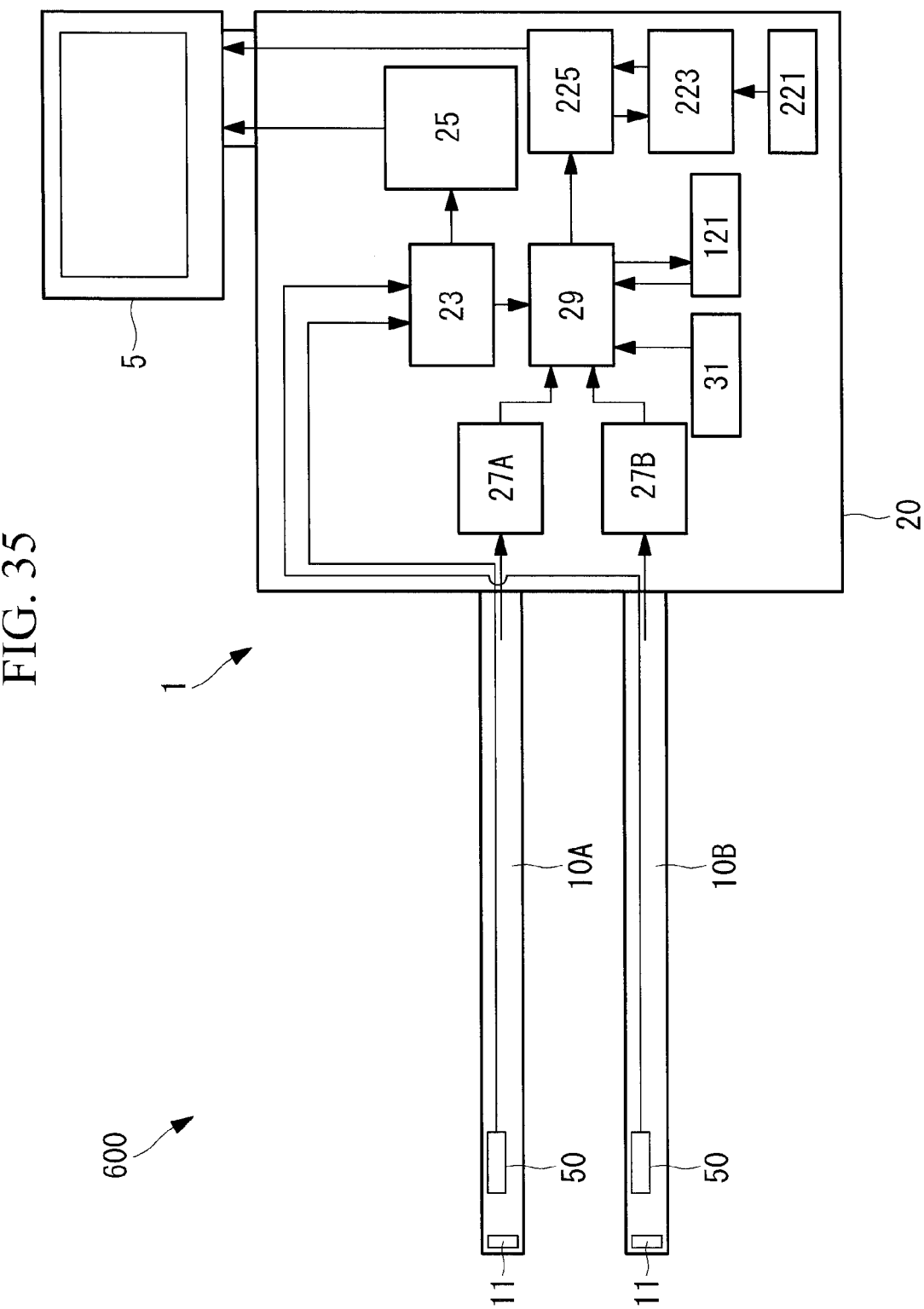
FIG. 35 is a configuration diagram illustrating, in outline, an endoscope device and a monitor of a medical system according to a modification of each of the embodiments of the present invention.
Figure 36:
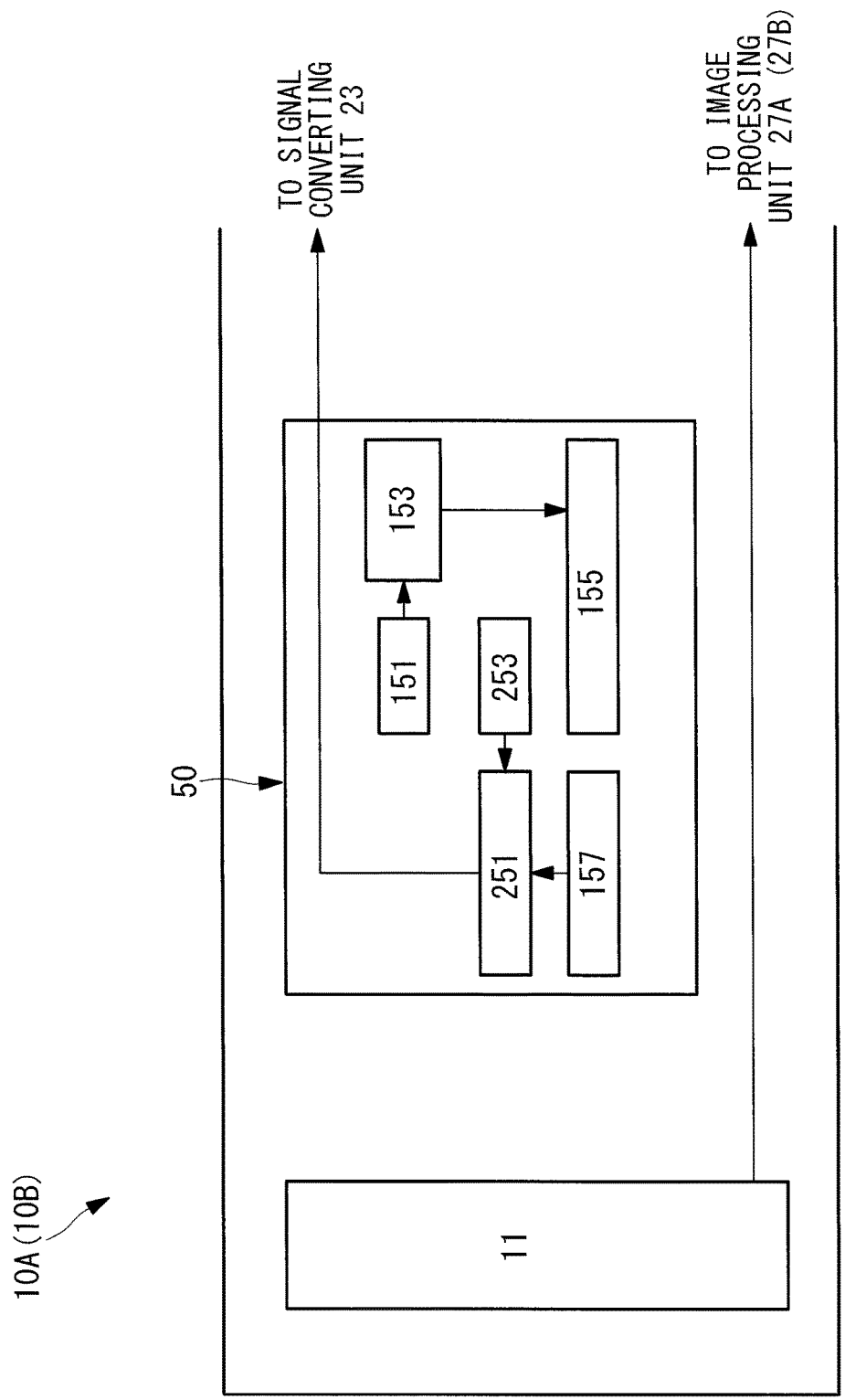
FIG. 36 is an enlarged diagram of the insertion portion in FIG. 34.

For example, as in a medical system 600 illustrated in FIGS. 35 to 37, the configuration may include identification-signal generating units 50 on the insertion portions 10A and 10B and an RFID tag 173 that can output a unique signal (of the sheath) on the sheath 40. Upon insertion of the insertion portion 10A or 10B into the sheath 40, the identification-signal generating unit 50 may detect the unique information of the sheath 40 and generate an identification signal, which is transmitted from the signal combining unit 251 to the signal converting unit 23 in the main unit 20 via the signal line in the insertion portion 10A or 10B.

In this way, an identification signal does not have to be wirelessly transmitted from the transmission antenna, and the signal does not have to be amplified; thus, power consumption decreases, and radio wave interference does not occur, enabling stable control.

REFERENCE SIGNS LIST 1 endoscope device (medical device)
3, 3A, 3B sheath unit (outer sleeve)
5 monitor (display unit)
10A, 10B insertion portion
13A, 13B barcode (identification-information generating portion)
20 main unit
29 image selector (control unit)
40a through-hole
50 identification-signal generating unit (identification-information output unit, outer-sleeve-information output unit)
51 LED light source (light source unit)
55 photodiode (detection unit)
100, 200, 300, 400, 500, 600 medical system
113A, 113B RFID tag (identification-information generating portion)
121, 325, 327 memory (storage unit)
315 illumination LED (illumination light source)
421 moving-image recording unit (image recording unit)
S biological subject

The invention claimed is:

1. A medical system comprising:
   an outer sleeve that has one end and another end, that has a through-hole formed from the one end to the another end, and that is attachable to the biological subject while the one end is inserted into the biological subject;
   a medical device including a plurality of insertion portions that are inserted into a body cavity in the biological subject through the through-hole and a main unit that supports the plurality of insertion portions;
   a display unit on which insertion-portion unique information serving as unique information of each insertion portion can be displayed;
   an identification-information generating portion that is provided on the insertion portions or the outer sleeve and issues insertion-portion identification information serving as identification information of each insertion portion; and
   an identification-information output unit that acquires the insertion-portion identification information issued from the identification-information generating portion every time the insertion portion passes through the through-hole and outputs the acquired information to the main unit,
   wherein the main unit includes a control unit that identifies the insertion portion passing through the outer sleeve on the basis of the insertion-portion identification information sent from the identification-information output unit and displays the insertion-portion unique information of the identified insertion portion on the display unit,
   wherein the medical device is a image acquisition device that acquires an image of the inside of the body cavity in the biological subject with the insertion portions, and
   the control unit displays the image acquired by the identified insertion portion as the insertion-portion unique information on the display unit,
   the main unit includes a storage unit that stores the insertion-portion identification information sent from the identification-information output unit and an image recording unit that records an image acquired by the insertion portion, and
   the control unit compares the insertion-portion identification information of a newly identified insertion portion with the insertion-portion identification information stored in the storage unit immediately before, records an image acquired by the newly identified insertion portion in the image recording unit if the insertion-portion identification information differs, and stops the recording performed by the image recording unit if the insertion-portion identification information matches.

* * * * *